United States Patent [19]

Nielsen et al.

[11] Patent Number: 5,078,782
[45] Date of Patent: Jan. 7, 1992

[54] PESTICIDAL CONCENTRATE COMPOSITIONS

[75] Inventors: Erik Nielsen, Greve Strand, Denmark; Sven Månsson, Lomma, Sweden

[73] Assignee: Berol Nobel (Suisse) S.A., Fribourg, Switzerland

[21] Appl. No.: 544,031

[22] Filed: Jun. 27, 1990

Related U.S. Application Data

[63] Continuation of Ser. No. 124,844, Oct. 9, 1987, abandoned.

[30] Foreign Application Priority Data

Apr. 24, 1986 [DK] Denmark .............................. 1913/86

[51] Int. Cl.$^5$ .................... A01N 25/30; A01N 25/22; A01N 25/00
[52] U.S. Cl. .................................... 71/100; 424/405; 424/409; 514/937
[58] Field of Search .................. 71/100; 424/405, 409; 514/937

[56] References Cited

U.S. PATENT DOCUMENTS

| | | | |
|---|---|---|---|
| 3,671,571 | 6/1972 | Koenig et al. | 560/29 |
| 4,460,406 | 7/1984 | Valange | 71/100 |

FOREIGN PATENT DOCUMENTS

| | | |
|---|---|---|
| 6348 | 1/1980 | European Pat. Off. . |
| 98561 | 1/1984 | European Pat. Off. . |
| 102003 | 3/1984 | European Pat. Off. . |
| 142670 | 5/1985 | European Pat. Off. . |
| 185185 | 6/1986 | European Pat. Off. . |
| 3324336 | 1/1984 | Fed. Rep. of Germany . |
| 2053631 | 4/1971 | France . |
| 892864 | 8/1982 | France . |
| 371081 | 1/1970 | Sweden . |
| 647929 | 10/1979 | Switzerland . |
| 1272407 | 4/1972 | United Kingdom . |
| 1300094 | 12/1972 | United Kingdom . |
| 2123294 | 2/1984 | United Kingdom . |
| WO2976 | 7/1985 | World Int. Prop. O. . |

OTHER PUBLICATIONS

Gruzden, G. S., ed., "Chemical Protection of Plants," Moscow, Kolos Publishers, 1980, pp. 332–333.

*Primary Examiner*—John W. Rollins
*Assistant Examiner*—Ralph Gitomer
*Attorney, Agent, or Firm*—Birch, Stewart, Kolasch & Birch

[57] ABSTRACT

A pesticidal concentrate comprising a pesticidal component suspended in an oily component, the composition comprising 1–55% by weight of pesticide, 20–90% by weight of the oily component and 1–45% by weight of a surfactant component, and optionally water and optionally filler, the surfactant component comprising one or more stabilizing constituents comprising a $C_{5-30}$ hydrocarbylene chain carrying a group capable of forming hydrogen bonds with water, and optionally one or more other constituents selected from the group consisting of non-ionic and ionic surfactants, the stabilizing constituent being present in an amount of at least 4% by weight, calculated on the total amount of surfactant component in the composition.

Examples of stabilizing constituents are fatty alcohols and amino group-containing surfactants, especially ampholytes.

Pesticidal concentrate compositions comprising 1–55% by weight of finely ground dithiocarbamate or glyphosate suspended in 10–90% by weight of an oily component and comprising 1–50% by weight of a surfactant component, calculated on the total composition, may be prepared.

The pesticidal concentrate compositions are used in the preparation of ready-to-use-spray liquid, normally comprising 0.1–10% of concentrate and 90–99.9% of water.

63 Claims, No Drawings

PESTICIDAL CONCENTRATE COMPOSITIONS

This application is a continuation of application Ser. No. 07/124,844 filed on Oct. 9, 1987, now abandoned.

BRIEF DESCRIPTION OF THE INVENTION

The present invention relates to a pesticidal concentrate composition in which the pesticide is dispersed in an oily component, the composition comprising 1–55% by weight of pesticide, 20–90% by weight of the oily component, and 1–45% by weight of a surfactant component, and optionally water and optionally filler, the surfactant component comprising one or more stabilizing constituents comprising a $C_{5-30}$ hydrocarbyl or hydrocarbylene chain carrying a group capable of forming hydrogen bonds with water, and optionally one or more other constituents selected from the group consisting of non-ionic and ionic surfactants, the stabilizing constituent being present in an amount of at least 4% by weight, calculated on the total amount of surfactant component in the composition. However, some pesticidal compositions, i.e. compositions comprising a dithiocarbamate or glyphosate, may be prepared with surfactant compositions which do not necessarily fulfil the above limitations with respect to the stabilizing constituent.

Pesticides to be used in the agriculture are normally marketed as liquid concentrates which are to be diluted with water before the final use so that they can be sprayed on fields or plants by means of conventional spraying equipment. During the dilution process with water before the final use and with stirring without special precautions the pesticidal component can move freely from the oily phase into the added aqueous phase when the oil is simultaneously emulsified into the water making an oil-in-water emulsion.

BACKGROUND OF THE INVENTION

Storage-stable aqueous suspensions of pesticides (flowables) to be diluted with water have been used to an increasing extent during recent years. Several environmental advantages are associated with products of that kind, e.g. in comparison to dispersible powder preparations there are no problems with dust and in comparison to emulsion concentrates in which the presticide is dissolved in a solvent which is emulsified in water by means of surfactants, it is possible to avoid the use of toxic and disagreeable solvents.

Another known type of pesticidal concentrate is an oil-containing pesticide suspension in which the oil is emulsifiable in water. When such a composition is diluted in water for the final use the emulsifier must be able to distribute the oil without forming gels or lumps and to distribute the pesticide in the aqueous phase. It is important that the distribution in the aqueous phase takes place quickly and without difficulties. As most field-spray equipments are nowadays equipped with effective impellers it is acceptable it is acceptable that a minor separation of oil or pesticide takes place on standing, but it is not acceptable if the oil gradually separates in such a manner that the pesticide is agglomerated into greasy layers or precipitates. The emulsifier used should also ensure that both oil and pesticide are distributed efficiently on the plants.

On standing most suspension concentrates normally tend to separate out so that a clear upper layer appears. Normally, this has no practical consequence, but if the suspension comprises both oil and water in one or two phases, both of these phases as well as the suspended phase of solid particles should be able to be shaken into a homogeneous slurry which will not separate immediately into separate fractions.

It is decisive that the surfactant composition in oil-containing compositions is active under different conditions. It is especially difficult to optimize the surfactant system if the amount of emulsifier is low and if the liquid phase is non-aqueous or if the water content is low, e.g. below 10%, especially below 3–5%, by weight. In these circumstances it may be difficult to distribute the oil-containing suspension in the aqueous phase without the forming of greasy precipitations comprising both oil and pesticide particles.

Oil-containing pesticidal dispersions can be advantageous compared to aqueous systems when the oil acts as activator in relation to the biological effect. A non-aqueous system or a system with a low water content will be preferred under circumstances in which water acts detrimentally on the stability, e.g., when water has an adverse effect on the chemical stability, promotes the development of toxic decomposition products and/or dissolves the finely suspended pesticidal active components.

Applicants' co-pending European application EP, A2, 142670 describes stabilized liquid herbicidal compositions comprising, as active ingredient, a herbicidally effective amount of carbamates such as phenmedipham, optionally in admixture with metamitron, in which the active ingredient in a finely ground state is dispersed in a liquid phase which comprises at least one oily component in an amount of 5–75% by weight, and at least one surfactant in an amount of 5–60% by weight, and optionally water. Example 15 of said patent application describes how solid, finely ground phenmedipham is suspended in either mineral oil-containing micro-emulsions or mixtures of organic solvents and mineral oil which in dilution with water form micro-emulsions. The concentration of the finely ground pesticide is decisive for the rate of dissolution. When this is sufficiently low, e.g. below 150 g/l, it is normally easier to mix the composition with water than when the concentration is higher which is seen by the fact that generally only a small separation of pesticide takes place when water is added.

Biological testing of phenmedipham-comprising compositions has shown that it is important that the content of oil is sufficiently high in order to achieve the biological effects of the oil-containing suspension concentrates when the tests are carried out not only in greenhouses but in field trials. Based on biological testing, it has been found that the liquid phase should preferably consist of oil and surfactant which activate the biological effect, i.e. the weed killing effect is increased when oil and/or surfactant is added to the composition.

When the pesticide is a herbicide and this herbicide is a mixture of phenmedipham and metamitron in the form of a suspension it is advisable that the content of mineral oil is high and that the content of water, organic solvents and surfactants is low as metamitron is much less soluble in mineral oil than in water and surfactant. A high solubility will normally lead to a physically unstable suspension.

Nowadays, it is normal practice for farmers to admix metamitron and phenmedipham compositions with water in tanks. Metamitron is normally marketed as a water dispersable powder preparation containing 70% by weight of metamitron, and phenmedipham is normally marketed as an emulsifiable preparation based on isophorone and with a content of active ingredient of 160 g/l. By mixing in tanks the degree of distribution of the products in the aqueous phase is normally decreased. As the phenmedipham-containing preparation containing emulsifier is preferably used in concentrations of about 1% by weight, a fast up-take of isophorone in the dilution water will take place and this will lead to crystallization of phenmedipham. It appears that the crystallization will take place on the suspended metamitron particles. In practice, this conversion can be seen by the fact that the slurried particles tend to sediment, and depending on the surfactant composition in the phenmedipham preparation there will also be a tendency to some flocculation.

Biological testing on weeds in beets has shown that oil-containing suspension concentrates comprising phenmedipham and metamitron have a surprisingly strong herbicidal effect if the active components are efficiently distributed in the aqueous phase. This must be due to the fact that then, there is no possibility for undesirable interactions in the dilution step, but the invention is not limited to this theory.

Metamitron is normally used in larger amounts than phenmedipham. Therefore, it is advisable that the concentration of metamitron in mixed preparations is 3-5 times as high as the concentration of phenmedipham. Therefore, the dosage per hectare will be higher, and compared to a preparation comprising only phenmedipham a larger volume of product must be used. In order that the amount spread on the fields is not too high it is important that the concentration of the active components is as high as possible. In the Examples in EP, A2, 142670 dealing with phenmedipham and metamitron in non-aqueous oil-containing suspensions, the total content of pesticide is about 250 g/l. It has been found that it would be advantageous to increase this amount so that the total amount of pesticide is at least 280 g/l, more preferably at least 300 g/l, e.g. 320 g/l. By using high concentrations it is possible to spread a lower amount of the final pesticidal composition on the fields, thus giving a benefit in application.

A high content of oil will increase the toxic influence on the plants. In compositions comprising metamitron a high content of water will normally act detrimentally on the storage stability. Hence, it is not possible to substitute a major part of the water for oil.

In the Examples of EP, A2, 142670 all surfactant compositions are combinations of ionic and non-ionic surfactants. In the Examples of the above-mentioned European patent application the main part of the ionic component(s) consists of anionic surfactants (dodecylbenzene sulphonic acid and esters of phosphoric acid) partially neutralized with a base. With surfactants of this type it has not been possible to prepare suspension compositions comprising 260 g/l of metamitron and 60 g/l of phenmedipham when the amount of oil is high, e.g. above 50-55% by weight, and the total amount of surfactant is low, e.g. below 10% by weight. In EP, A2, 142670 it is mentioned that ampholytes can be used as surfactants in oil-containing suspensions of phenmedipham. However, only 3% of the total amount of surfactant is a coco alkylamino propionic acid, and the amount of this compound constitutes only a minor amount, i.e. about 6% by weight of the total amount of ionic surfactants.

CH P 647929 (Schäfer et al.) describes pesticide compositions in which the active component is dissolved in an aqueous phase comprising at least one non-ionic surfactant and a ionic surfactant wherein the non-ionic surfactant has a HLB-value of 5-20 and the ionic surfactant component is an ampholyte, optionally in combination with an anionic or cationic surfactant. There is no mentioning of the use of oily substances.

DETAILED DESCRIPTION OF THE INVENTION

The present invention is based on the surprising fact that when the surfactant component comprises one or more stabilizing constituents comprising a $C_{5-30}$ hydrocarbyl or hydrocarbylene chain carrying a group capable of forming hydrogen bonds with water, and optionally one or more other constituents selected from the group consisting of non-ionic and ionic surfactants, and the stabilizing constituent is present in an amount of at least 4% by weight, calculated on the total amount of surfactants, it is possible to prepare liquid pesticidal compositions in the form of concentrates with a high content of pesticide which can be satisfactorily distributed in water.

The stabilizing constituent is not necessarily per se a conventional surfactant with emulsifying properties.

It is preferred that the stabilizing constituent comprises a hydrocarbyl or hydrocarbylene chain with 7-22, especially 9-18, carbon atoms. The group which is capable of forming hydrogen bonds with water can be an amino group or a hydroxy group. The hydroxy group is connected to the hydrocarbyl or hydrocarbylene chain.

Especially preferred stabilizing constituents which comprise a hydroxy group are compounds which further to the hydrocarbyl or hydrocarbylene chain carry only hydroxy groups. The number of hydroxy groups is at the most 2 and preferably 1. Even if the $C_{5-30}$ hydrocarbyl or hydrocarbylene alcohol could be considered an oily component, the amount of said alcohol is not incorporated in the amount of oily component. The amount of alcohol is incorporated in the surfactant component.

The amount of stabilizing constituent constitutes more than 4% by weight of the total amount of surfactant in the composition, preferably 6-60%, more preferably 8-45%, and especially 12-35%, by weight, calculated on the total amount of surfactant component in the composition.

A high content of oil in oil-containing compositions with a pesticide in suspended form is desirable in view of the fact that the biological activity is thereby increased, and for such oil-containing compositions one or more stabilizing constituent(s) is used in combination with non-ionic surfactants for emulsifying the oily phase in the water used for diluting the composition before the final use. When the surfactant component comprising one or more stabilizing constituent(s) is used in combination with preferably non-ionic surfactants very stable emulsions are formed after the dilution with water and, hence, the distribution in the field is made easier in that no greasy oily residues or flocculated pesticide are left in the spraying equipment.

In a preferred composition the stabilizing constituent or each stabilizing constituent comprises an amino group-containing surfactant which is a $C_{5-30}$, preferably a $C_{7-22}$, most preferably a $C_{9-18}$, hydrocarbyl or hydrocarbylene amine which is optionally substituted by one or more groups selected from carboxy, sulphonic acid groups, phosphonic acid groups, (poly)oxyalkylene and hydroxy groups and one or more further $C_{1-20}$-hydrocarbyl or hydrocarbylene groups which themselves may be substituted by the above-mentioned groups. The further $C_{1-20}$-hydrocarbyl or hydrocarbylene groups may comprise phenyl or phenylene groups. Aliphatic chains are preferred. An optionally substituting (poly)oxyalkylene group can be connected directly to the amino group or to the hydrocarbyl or hydrocarbylene chain.

Amino group-containing surfactants are suited for the formulation of pesticidal compositions wherein the pesticide is suspended in an oily component, when the compositions are acidic because of the physical and chemical stability of the pesticidal composition in question (e.g. in the case of glyphosate which is decomposed at alkaline pH's) or when a low content of surfactant component is preferred for reasons of phytotoxity (e.g. in the case of a fungicide such as maneb to be used mainly on potatoes).

The amino group-containing surfactants are in combination with non-ionic surfactants able to produce very storage-stable suspensions of the dispersed pesticides in the oily phase, which means that the pesticide will normally not settle and form a sediment which cannot be redispersed. Even if the composition according to the invention has a very low content of water the suspended pesticide will have only a low tendency to settle with a surfactant mixture as described above.

A surfactant component combined as described above may also be used in highly viscous compositions.

During the mixing process in which the pesticidal composition is diluted with water, the viscosity will, with unmodified compositions, greatly increase, which means that the mixing process can only proceed slowly. However, the rate of mixing can be increased considerably if the surfactant component comprises at least two different amino group-containing surfactants as defined above of which at least one in addition to the amino group carries at least one further group selected from carboxy, sulphonic acid groups, phosphonic acid groups, (poly)oxyethylene, (poly)oxypropylene and hydroxy groups and one or more further $C_{1-20}$-hydrocarbyl or hydrocarbylene groups which themselves may be substituted by the above-mentioned groups. The further $C_{1-20}$-hydrocarbyl or hydrocarbylene groups may comprise phenyl or phenylene groups. Aliphatic chains are preferred.

It is especially preferred that the two different amino group-containing members carry different groups.

It is preferred that the stabilizing constituent does not comprise a phosphate ester group.

It has been found that the rate of mixing is increased if the composition comprises an ethoxylated, propoxylated and/or co-ethoxylated/propoxylated hydrocarbyl or hydrocarbylene amine and/or hydrocarbyl or hydrocarbylene-di-, -tri- or -polyamine and at least one further amino group-containing surfactant which carries at least one carboxy group, or if the composition comprises an ethoxylated, propoxylated and/or coethoxylated/propoxylated hydrocarbyl or hydrocarbylene amine and/or hydrocarbyl or hydrocarbylene-di-, -tri- or -polyamine and at least one further amino group-containing surfactant which carries at least one sulphonic acid group.

It is especially preferred that the amino group-containing surfactant comprises an amino group and a carboxy group. The term "ampholyte" used hereinafter designates an amino group-containing surfactant substituted by a carboxy group. Ampholytes may also comprise other groups such as hydroxy and (poly)oxyalkylene.

Hydrocarbyl designates a radical consisting of only hydrogen and carbon and as examples of hydrocarbyl radicals may be mentioned alkyl radicals, alkenyl radicals, alkynyl radicals, alkynyl radicals and aryl radicals, e.g. nonyl, oleyl, pentynyl, and benzyl. The term hydrocarbylene similarily designates a bivalent radical comprising only carbon and hydrogen.

The amino group in the amino group-containing surfactant can be a primary, a secondary or a tertiary amino group. The amino group may also be quaternarised, but this is not preferred.

The amino group-containing surfactant should be dissolved or dispersed in the oily component.

The amino group-containing surfactant should not, per se, be a pesticide.

As examples of ampholytes which are useful in oily suspensions may be mentioned N-alkyl-$\beta$-amino propionic acids (wherein alkyl designates groups of 5-30, preferably 7-22 and more preferably 9-18 carbon atoms), N-alkyl N-dimethylamino acetic acid (betaine) and imidazolin-amphotensides such as compounds of the formulae

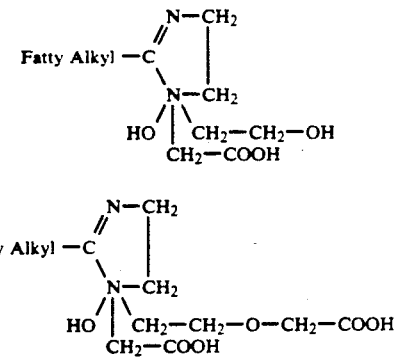

and carboxymethylated and ethylated derivatives of the formulae

CARBOXYMETHYLATED DERIVATIVES

Monocarboxylic acid

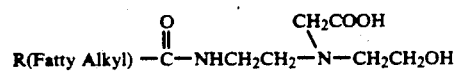

Dicarboxylic acid

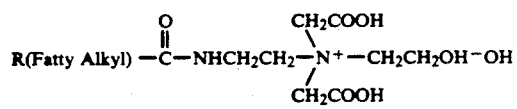

CARBOXYETHYLATED DERIVATIVES

Monocarboxylic acid

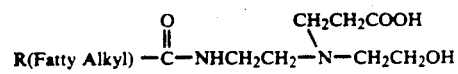

Dicarboxylic acid

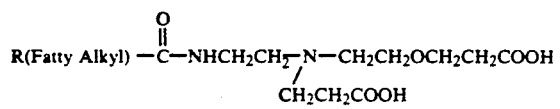

wherein Fatty Alkyl is $C_{5-30}$, preferably $C_{7-22}$ and more preferably $C_{9-18}$ alkyl.

If the stabilizing constituent is an amino group-containing surfactant or surfactants (including ampholytes), it is preferred that the amount of amino group-containing surfactant constitutes at least 50%, more preferably 70%, and especially at least 90%, most preferably 100%, calculated on the total amount of the ionic surfactant constituent or constituents. The amino group-containing surfactant is considered a ionic surfactant, also if it is polyoxyalkylated, even if the number of oxyalkylene groups per molecule of amino is high.

It will often be advantageous (in order to secure stability of the composition and/or the chemical stability of pesticides) that the amino group in the amino group-containing surfactant is activated by an acid. Therefore, it is often advisable to add a strong acidic component to the pesticidal composition. As acidic components may be mentioned members from the group consisting of strong inorganic acids, strong organic acids, acid chlorides, and acid anhydrides. As strong mineral acids may be mentioned hydrochloric acid, hydrobromic acid, hydroiodic acid, sulfuric acid, nitric acid, phosphoric acid, and preferably perchloric acid. As strong organic acids may be mentioned acids selected from the group consisting of aliphatic and aromatic di-, tri- and tetracarboxylic acids, aliphatic and aromatic hydroxy carboxylic acids, aliphatic and aromatic carboxylic acids substituted by one or more halogen atoms, aliphatic and aromatic nitrocarboxylic acids, aliphatic and aromatic sulphonic acids, and phosphoric acid partially esterified with optionally ethoxylated lower alcohols. Especially preferred organic acids are aliphatic dicarboxylic acids such as maleic acid, fumaric acid, and succinic acid and anhydrides and chlorides thereof. In itself, the acidic component should not normally have surfactant properties.

When acidic components are present in the composition, this acidic component is normally used in an amount of 25-400% on a molar basis, preferably 50-250% and especially 100-175%, calculated on the amount of the amino group-containing stabilizing surfactant constituent or constituents. It is preferred that pH is in the range of 2-4, preferably about 3, in the pesticidal composition.

If the suspended pesticide has a relatively low purity or if the pesticide is difficult to disperse in the oily component, the composition may tend to separate and the viscosity may tend to increase so that the total composition becomes a greasy, incoherent mass. This unfavourable behaviour is avoided when the stabilizing constituent comprises a $C_{5-30}$-fatty alcohol such as nonanol or decanol in an amount of 0.2-20% by weight, preferably 1-10% by weight, especially 2-6% by weight, based on the total composition. This fatty alcohol being a part of the surfactant component and being present in an amount of at least 4% by weight of the total amount of surfactant in the composition, preferably 6-60%, more preferably 8-45%, and especially 12-35%, by weight, calculated on the total amount of surfactant component in the composition.

The use of fatty alcohols as stabilizing constituent in the pesticidal concentrate compositions is especially advantageous in systems in which the amount of surfactant component is high. The fatty alcohol reduces viscosity, increases the rate of mixing in water and stabilizes the storage stability.

It is especially preferred to incorporate a non-ionic surfactant in the surfactant component in the pesticidal compositions according to the invention. The non-ionic surfactants can be selected from the group consisting of block polymers which are condensates of polyoxyethylene and polyoxypropylene; ethoxylated, propoxylated or co-ethoxylated/propoxylated fatty alcohols; ethoxylated, propoxylated or co-ethoxylated/propoxylated mono-, di- or trialkyl phenols.

If the pH in the composition is not too low, (i.e. so low that it causes hydrolysis of the esters), mono-, di- or poly(carboxyl) fatty acid esters may be used (preferably esters of $C_8$–$C_{22}$ alkyl fatty acids) in which the alcohol moiety is selected from the group consisting of polyoxyethylene alcohol, polyoxypropylene alcohol, polyoxyalkylene alcohols combined from different glycols, polyalcohols, and ethoxylated, propoxylated and co-ethoxylated/propoxylated polyalcohols.

It will often be advantageous to use a combination of two non-ionic surfactants which are different and have different HLB values, e.g. with HLB values of 6 and 11. (HLB = Hydrophilic-Lipophilic-Balance; HLB values are theoretical, calculated values used in connection with ethoxylated non-ionic detergents. The HLB is directly proportional to the content of polyethylene oxide. HLB values are between 0 and 20; a low HLB indicates an oil-soluble surfactant, and the water-solubility increases with increasing HLB values).

The pesticidal compositions may optionally comprise varying amounts of water. The stability of the active components can be decisive for the amount of water present. Pesticidal compositions may be non-aqueous or comprise water in amounts of 0.1-15% by weight or even more, i.e. up to 40% by weight. Hence, the compositions may comprise water in an amount of 0.1-40%, preferably, 0.2-20%, especially 0.5-10% and more especially 1-5%, by weight, based on the total composition. Often, the ingredients will be used in wet form.

The pesticides used in the compositions according to the invention may be solid or liquid. When the pesticide is solid, the oil-comprising pesticide dispersion may be prepared by mixing the coarsely ground pesticide(s) in the whole amount of the liquid oily phase (containing the surfactants) or in a part thereof.

The pesticidal components in the oily phase may be subjected to a grinding a wet state in a bead mill with beads of a size of 0.5-3 mm, preferably 1 mm. In production scale the grinding may be performed on a mill, such as a Dyno TM mill. After the grinding process, the remaining part, if any, of the oily phase is added. The grinding process may be carried out to such an extent that 50% by weight of the finely ground pesticide particles (weight basis) have a particle size of less than $20\mu$, preferably less than $10\mu$ and more preferably of less than $5\mu$. The particle size may be determined on a Malvern Particle sizer 3600 E Type using low power laser light diffraction technique. In order to obtain a correct result the particular pesticide particles must not be agglomerated by the liquid oily phase in the dilution used.

In order to suppress the tendency to separate a compact pesticide sediment during storage of the suspension it may be advantageous to add a filler. As examples of fillers may be mentioned natural and synthetic clays and silicates, e.g. natural silicas such as diatomaceous earths; magnesium silicates, e.g. talcs; magnesium aluminium silicates, e.g. attapulgites and vermiculites; aluminium silicates, e.g. kaolinites, montmorillonites and micas; synthetic hydrated silicon oxide units and synthetic calcium or aluminium silicates; natural and synthetic resins, such as e.g. coumarone resins, polyvinyl chloride and styrene polymers and copolymers; and solid fertilisers, e.g. superphosphates. Inorganic fillers are preferred. Especially preferred are fillers such as bentonite and hectorite and organic derivates thereof such as Bentone TM. If a filler is incorporated in the pesticidal composition the amount thereof will be 0.1–15% by weight, preferably 0.2–10% by weight, especially 0.5–5% by weight and more preferably 1–3% by weight. In addition to the separation-suppressing activity, an added filler will often also improve the grinding of the pesticidal component, especially if the grinding is performed in wet state in bead mill. If the inorganic filler is added after the grinding process it will act more sedimentation-suppressing. This is especially marked when the filler is needle-formed crystals as is the case with attapulgite.

In the pesticidal concentrate composition according to the present invention the pesticidal component is suspended in an oily component, the composition comprising 1–55%, preferably 5–50%, more preferably 10–40% and most preferably 15–35%, by weight of pesticide, 20–90%, preferably 33–80%, more preferably 40–75% and most preferably 45–70%, by weight of the oily component, 1–45%, preferably 2–30%, more preferably 3–25% and most preferably 4–20%, by weight of a surfactant component, and optionally water and optionally filler, the surfactant component comprising one or more stabilizing constituent(s) comprising a $C_{5-30}$, preferably a $C_{7-22}$, more preferably a $C_{9-18}$, hydrocarbyl or hydrocarbylene chain carrying a group capable of forming hydrogen bonds with water, and optionally one or more other constituents selected from the group consisting of non-ionic and ionic surfactants, the stabilizing constituent being present in an amount of at least 4% by weight, calculated on the total amount of surfactant component in the composition. The pesticidal component may be a mixture of one or more pesticides which may be solid and/or liquid at normal temperatures.

In one type of pesticidal compositions, the pesticidal component may be a mixture of pesticides in which at least one of the pesticides is a liquid at normal temperature and insoluble in the oily component. Hence, a preferred pesticidal composition is a composition in which at least one of the pesticides, which at normal temperature is liquid and insoluble in the oily component, is suspended in an oily component, the composition comprising 1–55%, preferably 5–50%, more preferably 10–40% and most preferably 15–35%, by weight of pesticide, 20–90%, preferably 33–80%, more preferably 40–75% and most preferably 45–70%, by weight of the oily substance, 1–45%, preferably 2–30%, more preferably 3–25% and most preferably 4–20%, by weight of a surfactant component, and optionally water and optionally filler, the surfactant component comprising one or more stabilizing constituents comprising a $C_{5-30}$ hydrocarbyl or hydrocarbylene chain carrying a group capable of forming hydrogen bonds with water, and optionally one or more other constituents selected from the group consisting of non-ionic and ionic surfactants, the stabilizing constituent being present in an amount of at least 4% by weight, calculated on the total amount of surfactant component in the composition.

The oily component is suitably a water-insoluble substance selected from the group consisting of petroleum fractions (hydrocarbons), vegetable oils, and esters of monoalcohols or of dihydric, trihydric or other lower (e.g. 4–6 hydroxy functions) polyalcohols, and esters of mono-, di- and polycarboxylic acids, and mixtures thereof. As examples of petroleum fractions may be mentioned mineral oils, such as spindle oil and aromatic compounds such as propylbenzene and dodecylbenzene, paraffinic oils, etc.; as examples of vegetable oils may be mentioned soy oil, rape seed oil, olive oil, etc.; as an example of esters of alcohols may be mentioned 2-ethyl hexyl stearate, n-butyl oleate, isopropyl myristate, propylene glycol dioleate, di-octyl succinate, di-butyl adipate, and di-octyl phthalate. Oily components are furthermore compounds which fulfill each of the conditions that they should be liquid at normal temperatures, be immiscible with water in a ratio of 1:10–10:1 by weight, comprise at least 67% by weight of hydrocarbyl or hydrocarbylene, calculated on the total chemical composition thereof. Oily components are components with a boiling point of at least 130° C., preferably at least 200° C., more preferably at least 250° C.

The oily component should preferably be a mineral oil with a low content of aromatics. The oily component may be a mineral oil with a content of aromatics of at the most 25% by weight, preferably at the most 10% by weight. The viscosity of the oily component should be less than 100 cSt at 40° C.

In the oily component, organic solvents may be added, e.g. glycols such as propylene glycol, and glycol ethers, such as butyl glycol.

The oily component may contain pesticides in dissolved form. As examples of oil-soluble pesticides may be mentioned S-2,3,3-trichloroallyl di-isopropyl(thiocarbamate) (tri-allate) and 3,6-dichloropyridine-2-carboxylic acid (3,6-dichloropicolinic acid). Interesting combinations comprising soluble herbicides are combinations comprising esters of (±)-2[4-(5-trifluoromethyl-2-pyridyloxy)phenoxy]propionic acid (Fluazifop) such as the butyl ester thereof (Fluazifop butyl) and esters of (±)-2[4-(3-chloro-5-trifluoromethyl-2-pyridyloxy)-phenoxy]propionic acid (Dowco 453) such as the ethoxyethyl ester thereof.

The pesticide dispersed in the pesticidal composition may be a mixture of one or more pesticidal components.

The nature of the oily component determines whether the pesticidal component or part thereof is dissolved or dispersed in the oily component. Tri-alleate, for example, is soluble in most aromatic hydrocarbon, but it is so slightly soluble in aliphatic hydrocarbons that it will substantially be dispersed therein. At least part of the pesticidal components must be in solid form which can be dispersed in the oily component.

The pesticidal component may be a herbicide, especially for use in beet fields. Usable herbicides are derivatives of urea, carboxylic acid ester, amino-acids, diphenylethers, phenylcarbamates, s-triazine, as-triazinones, heterocycles, s-triazindiones, phenylpyridazinones, benzofuran, quinoline carboxylic acids, phenoxy acetic acids, phenoxy propionic acids, and benzene sulphonamides.

Examples of herbicidally active ureas are:
3-(3-chloro-p-tolyl)-1,1 dimethylurea (Chlortoluron),
3-(4-isopropylphenyl)-1,1 dimethylurea (Isoproturon),
3-(3,4-dichlorophenyl)-1-methoxy-1-methylurea (Linuron),
1-(benzothiazol-2-yl)-1,3-dimethylurea (Methabenzthiazuron), and
3-(3-chloro-4-methoxyphenyl)-1,1-dimethylurea (Metoxuron).

Examples of herbicically acitive carboxylic acid esters are:
ethyl N-benzoyl-N-(3,4-dichlorphenyl)-DL-alaninate (Benzoylprop-ethyl),
isopropyl N-benzoyl-N-(3-chloro-4-fluorophenyl)-DL-alaninate (Flamprop-isopropyl), and methyl N-benzoyl-N-(3-chloro-4-flurophenyl)-DL-alaninate (Flamprop-methyl),
esters of (±)-2-[4-(3-chloro-5-trifluoromethyl-2-pyridyloxy)phenoxy]propionic acid (Dowco 453),
esters of (±)-2-[4-(6-chlorobenzothiazol-2-yloxy)-phenoxy]propionic acid (Fenthiaprop), such as the ethyl ester (Fenthiaprop-ethyl)
esters of (±)-2-[4-(6-chlorobenzoxazol-2-yloxy)phenoxy]propionic acid (Fenoxaprop), such as the ethyl esters (Fenoxaprop-ethyl),
(±)-2-[4-3,5-dichloro-pyridyloxy)phenoxy]propionic acid-2-benzyloxy-esters,
methyl 3-[1-(allyloxyimino)butyl]-4-hydroxy-6,6-dimethyl-2-oxocyclohex-3-ene carboxylate (Alloxydim) and lower esters of phenoxy acetic acid and phenoxy propionic acid such as 2,4-D, MCPA, Dichlorprop and Mecoprop.

Examples of herbicidally active amino acids are:
N-(phosponomethyl)glycine (Glyphosate) as acid or in salt form, and
(±)-2-amino-4-(hydroxymethylphosphinyl)butanoic acid (Glufosinate) as acid or in salt form.

Examples of herbicidally active diphenylethers are:
2,4-dichlorophenyl-4-nitrophenyl ether (Nitrofen), and
5-(2-chloro-α,α,α-trifluoro-p-tolyloxy)-2-nitrobenzoic acid (Acifluorfen).

Examples of herbicidally active phenylcarbamates are:
3-[(methoxycarbonyl)amino]phenyl-N-(3'-methylphenyl)carbamate (Phenmedipham), and
ethyl 3-phenylcarbamoyloxyphenylcarbamate (Desmedipham).

Examples of herbicidally active s-triazines are:
2-(4-chloro-6-ethylamino-1,3,5-triazin-2-ylamino)-2-methylpropioni-trile (Cyanazine),
2-chloro-4,6-bis(ethylamino)-1,3,5-triazine (Simazine),
2-tert-butylamino-4-ethylamino-6-methylthio-1,3,5-triazine (Terbutryne), and
2-chloro-4-ethylamino-6-isopropylamino-1,3,5-triazine (Atrazine).

Examples of herbicidally active as-triazin-5-ones are:
4-amino-4,5-dihydro-3-methyl-6-phenyl-1,2,4-triazin-5-one (Metamitron),
6-tert-butyl-4-isobutylideneamino-3-methylthio-1,2,4-triazin-5(4H)-one (Isomethiozin), and
4-amino-6-tert-butyl-4,5-dihydro-3-methylthio-1,2,4-triazin-5-one (Metribuzin).

An example of herbicidally active heterocyclic compounds is:
3-isopropyl-1(H)-benzo-2,1,3-thiadiazin-4-one-2,2-dioxid (Bentazone).

An example of herbicidally active s-triazindiones is:
3-cyclohexyl-6-dimethylamino-1-methyl-1,3,5-triazine-2,4(1H,3H)-dione (Hexazinone).

An example of herbicidally active sulfonamides is:
1-(2-chlorophenylsulphonyl)-3-(4-methoxy-6-methyl-1,3,5-triazine-2-yl)urea (Chlorsulfuron).

An example of herbicidally active phenylpyridazinones is:
5-amino-4-chloro-2-phenyl-3(2H)pyridazinone (Chloridazon).

An example of herbicidally active benzofurans is:
(±)-2-ethoxy-2,3-dihydro-3,3-dimethylbenzofuran-5-yl methanesulphonate (Ethofumesate).

Examples of herbicidally active phenoxy acetic acids and phenoxy propionic acids are:
2,4-dichlorophenoxy acetic acid (2,4-D)
4-chloro-2-methylphenoxy acetic acid (MCPA)
(±)-2-(2,4-dichlorophenoxy)propionic acid (Dichlorprop)
(±)-2-(4-chloro-2-methylphenoxy)propionic acid (Mecoprop) and
(±)-2-[4-(4-chlorophenoxy)phenoxy]propionic acid.

In compositions comprising the above-mentioned active acids, at least part of the acids may be present in salted form.

An example of herbicidally active quinoline carboxylic acids is:
7-chloro-3-methyl-quinoline-8-carboxylic acid (BASF 518H).

An especially interesting pesticidal composition is a herbicide composition wherein the herbicidal component is selected from the group consisting of phenmedipham and metamitron, especially a composition comprising a mixture of phenmedipham and metamitron.

The weight ratio between phenmedipham and metamitron is preferably in the range of 1:2-1:8, more preferably in the range of 1:3-1:6, especially about 1:4.

In another aspect of the invention the pesticidal composition comprises a fungicide. The fungicidally active component may be a dithiocarbamate such as a (polymeric) manganese ethylenebis(dithiocarbamate) (maneb), (polymeric) zinc ethylenebis(dithiocarbamate) (zineb), (polymeric) manganese and zinc ethylenebis(dithiocarbamate) (mancozeb), and (polymeric) zinc propylenebis(dithiocarbamate) (propioneb). Other fungicidally active components are 2-benzimidazole carbamates, such as methyl benzimidazol-2-ylcarbamate (carbendazim) and methyl 1-(butylcarbamoyl)benzimidazol-2-ylcarbamate (benomyl). Other fungicidally active components are di-thioureido benzene derivatives such as 1,2-di(3-methoxycarbonyl-2-thioureido)-benzene (thiophanate-methyl) and 1,2-di(3-ethoxycarbonyl-2-thioureido)benzene (thiophanate).

In another aspect of the invention the pesticidal composition comprises an insecticide as the pesticidal component.

An interesting aspect of the invention relates to pesticidal compositions comprising one or more suspended pesticides in an amount of 1–55% by weight, preferably 5–50% by weight, more preferably 10–40% by weight, especially 15–35% by weight, such as 32% by weight of the total composition, formulated with an oily component such as mineral oil, e.g. spindle oil in an amount of 20–90%, preferably 33–80%, especially 40–75%, more preferably 45–70% by weight such as about 60% by weight of the total composition, a surfactant component in an amount of 1–45% by weight, preferably 2–30% by weight, especially 3–25% by weight, more preferably 4-20% by weight, such as 5-12% by weight, e.g. about 8% by weight of the total composition which further comprises at least one amino group-containing surfactant which further to the content of $C_{5-30}$ hydrocarbyl or hydrocarbylene comprises at least one further functional group selected from carboxy, sulphonic acids, phosphonic acids, (poly)oxyethylene, (poly)oxypropylene and hydroxy, in an amount of at least 4%, preferably 6-60%, especially 8-45% and more preferably 12-35% by weight, such as 19% by weight, calculated on the total amount of surfactant in the composition. Calculated on basis of the total composition the amino group-containing surfactant(s) may e.g. constitute 0.9-40% by weight, preferably 1-20% by weight, especially 1.2-10% and more preferably 1.5-5% by weight. The other constituents in the surfactant component will normally be constituted by one or more non-ionic surfactants, preferably having HLB values in the range of 4-12. The pesticidal composition may be stabilized with a strong acidic component, and the mixture may optionally comprise water and/or filler.

An interesting herbicidal composition according to the invention for use in beet field comprises 1-55% suspended phenmedipham, preferably 5-50%, more preferably 10-40%, and most preferably 15-35% by weight of the total composition, or 1-55% suspended metamitron, preferably 5-50%, more preferably 10-40%, most preferably 15-35% by weight of the total composition or a mixture of these in the amounts mentioned, e.g. 6% phenmedipham and 26% metamitron suspended in a mineral oil mixture, especially a mixture comprising mineral oil (having a content of aromatics of less than 10%) in an amount of 20-90%, preferably 33-80%, more preferably 40-75% and most preferably 45-70%, e.g. about 46% of a mineral oil with a low content of aromatics and with a viscocity of 20 cSt at 40° C., and about 10% of a petroleum fraction with a boiling point of 190°-240° C., calculated on the weight of the total composition, a non-ionic surfactant containing one or more ethoxylated, propoxylated or co-ethoxylated/propoxylated $C_{5-30}$-fatty alcohols; ethoxylated, propoxylated or co-ethoxylated/propoxylated mono-, di- or trialkyl phenols, which e.g. comprises 3-10 oxyethylene units, and in which the alkyl group comprises 6-20 (for fatty alcohol) and 4-15 carbon atoms (for alkylated phenols), especially 6-12 carbon atoms, and optionally an ethoxylated dialkyl phenol, which may e.g. comprise 4-14 oxyethylene units and in which the alkyl group comprises 4-15, preferably 6-12 carbon atoms and in which the surfactant component further comprises at least one amino group-containing surfactant with at least one hydrocarbyl or hydrocarbylene chain with 5-30 carbon atoms, preferably 7-22 carbon atoms and especially 9-18 carbon atoms, and at least one carboxy group and/or sulphonic acid group and/or phosphonic acid group, such as coco alkyl-β-amino propionic acid, and wherein the total amount of surfactant component constitutes 1-45%, preferably 2-30%, more preferably 3-25%, most preferably 4-20% and especially 5-12% by weight of the total composition, and the amino group-containing composition constitutes at least 4%, preferably 6-60%, more preferably 8-45% and especially 12-35%, e.g. 19%, by weight of the total amount of surfactant. The mixture may be further stabilized by a strong acidic component, e.g. perchloric acid in an amount of 0.1-10%, preferably 0.2-5% and more preferably 0.5-3%. If maleic acid anhydride is used as the strong acidic component, minor amounts such as 0.1-6%, preferably 0.2-2% such as 0.3% by weight will be sufficient.

Optionally, the mixture may be further stabilized by addition of water, e.g. i an amount of 0.5-5% by weight, based on the composition, and/or filler. pH in the composition is preferably 2-4, e.g. about 3.

As mentioned above, the rate of mixture with water for the preparation of the ready-to-use mixture to be spread on the fields may be improved considerably if the surfactant composition comprises various amino group-containing surfactants each of which further to the content of hydrocarbyl or hydrocarbylene comprises at least one further functional group. It has been found to be advantageous if the composition comprises an ethoxylated, propoxylated and/or coethoxylated/-propoxylated hydrocarbyl or hydrocarbylene amine and/or a hydrocarbyl/hydrocarbylene di-, tri- or polyamine and moreover at least another amino group-containing surfactant which besides the content of hydrocarbyl or hydrocarbylene comprises at least one carboxy group and/or a sulphonic acid group and/or a phosphonic acid group. It has been shown that under certain circumstances, such a combination renders the addition of an activating strong acidic component superfluous.

A surfactant component comprising various amino group-containing surfactants, but without any activating strong acids, is especially suitable for use in pesticidal compositions in which the pesticide comprises a dithiocarbamate in suspended form.

One aspect of the invention relates to pesticidal compositions comprising one or more suspended pesticides in an amount of 1-55% by weight, preferably 5-50% by weight, more preferably 10-40% by weight, especially 15-35% by weight, such as 32% by weight, calculated on the total composition, formulated with an oily component such as mineral oil, e.g. spindle oil in an amount of 20-90% by weight, preferably 33-80% by weight, more preferably 40-75% by weight, and especially 45-70% by weight, such as about 60% by weight, based on the total composition, a surfactant component in an amount of 1-45% by weight, preferably 2-30% by weight, more preferably 3-25% by weight, most preferably 4-20% and especially 5-12% by weight, such as 8% by weight, based on the total composition, said composition comprises an amino group-containing surfactant which further to the hydrocarbyl or hydrocarbylene content comprises at least one oxyalkylene group which can be mono-, di- or polyoxyethylene, mono-, di- or polyoxypropylene or a copolymerisate of ethylene oxide and propylene oxide in which the oxyalkylene group(s) is/are connected directly to the amino group and also a further amino group-containing surfactant which further to the hydrocarbyl or hydrocarbylene content comprises at least one further functionality, e.g. a carboxy, a sulphonic acid group, a phosphonic acid group or a hydroxy group, the total amount of surfactants containing amino groups constitutes at least 4% by weight, preferably 6-60% by weight, especially 8-45% by weight, and more preferably 12-35% by weight, such as 26% by weight, calculated on the total amount of surfactant. The remaining part of the surfactant will normally be constituted by one or more non-ionic detergents, preferably detergents with HLB values of 4-12. The pesticidal composition may be stabilized with a strong acidic component but this is not always desirable. The pesticidal composition may be formulated with or without water. The amount of water may constitute 0.1–15% by weight, preferably 0.5–5% by weight. In rare cases, the amount of water may be larger than 15% by weight. Normally, the mixture can be physically stabilized by means of an inorganic filler.

An interesting herbicidal composition according to the invention for use in beet fields is a composition comprising 1–55% of suspended phenmedipham, preferably 5–50%, more preferably 10–40% and most preferably 15–35%, by weight of the total composition, or 1–55% of suspended metamitron, preferably 5–50%, more preferably 10–40% and most preferably 15–35%, by weight of the total composition or a mixture of these in the amounts mentioned, e.g. 6% phenmedipham or 26% metamitron suspended in a mineral oil, especially a mineral oil (having a content of aromatics of less than 10%) in an amount of 20–90%, preferably 33–80%, more preferably 40–75% and most preferably 45–70%, e.g. about 46% mineral oil with a low content of aromatics and with a viscocity of 20 cSt at 40° C. and further containing about 10% of another petroleum fraction with a boiling point of 190°–240° C., all percentages being calculated on the weight of the total composition, a non-ionic surfactant comprising one or more ethoxylated, propoxylated or co-ethoxylated/-propoxylated fatty alcohols; ethoxylated, propoxylated or co-ethoxylated/propoxylated mono-, di- or trialkylated phenols, which e.g. comprises 3–10 oxyethylene units, and in which the alkyl group comprises 6–20 (for fatty alcohols) or 4–15 (for alkylated phenols), especially 6–12 carbon atoms, and optionally an ethoxylated dialkyl phenol, which may e.g. comprise 4–14 oxyethylene units and in which the alkyl groups comprise 4–15, preferably 6–12 carbon atoms, the surfactant components comprises at least one alkyl amine which is ethoxylated, propoxylated or co-ethoxylated/propoxylated, and in which the hydrocarbyl or hydrocarbylene chain preferably contains 5–30 carbon atoms, more preferably 7–22 carbon atoms, especially 9–18 carbon atoms, and the oxyalkylene chain is preferably a polyoxyethylene chain with 3–25, preferably 6–20 oxyethylene units, e.g. a coco alkylamine with 10 oxyethylene units, and in which the surfactant component comprises at least one amino group-containing surfactant with at least one $C_{5-30}$-hydrocarbyl or hydrocarbylene chain, preferably with 7–22 carbon atoms, more preferably 9–18 carbon atoms, and which carries at least one carboxy group and/or sulphonic acid group, e.g. coco alkyl-$\beta$-amino propionic acid, and wherein the total amount of surfactant component constitutes 1–45%, preferably 2–30%, more preferably 3–25%, most preferably 4–20% and especially 5–12% by weight of the total composition, and so that the amino group-containing surfactant constitutes at least 4%, preferably 6–60%, more preferably 8–45% and especially 12–35%, e.g. 27%, by weight of the total amount of surfactant, and in which the pesticidal composition may be further stabilized by maleic acid or maleic acid anhydride e.g. in an amount of 0.1–1%, or in which the pesticidal composition is stabilized by perchloric acid, e.g. in an amount of 0.2–3% by weight of the total composition. The composition may further comprise water and fillers. pH in the compositions is preferably 2–4, e.g. about 3.

In recent years many attempts have been made to prepare stable suspensions of maneb (a dithiocarbamate) in water. However, there are no favourable commercialized products. The problem lies in the difficulties in rendering the suspensions sufficiently storage stable. Maneb is a high density solid which in suspended form in water has a tendency to sediment and form precipitations which are very difficult to re-disperse. Furthermore, in the presence of water, the very toxic compound ethylene thiourea is formed. After storage for one year a content of ethylene thiourea of 2% can be found.

It is surprising that if a suspension is made up in an oily component instead of water, there is not only a very small demonstratable content of ethylene thiourea, but a decrease in the content thereof takes place. The reason may be that reversible reactions take place when the ethylene thiourea is formed.

It is known to combat lice which may cause potato virus Y (crinkle) by spraying, on the potato fields, a composition comprising maneb and an emulsifiable mineral oil in amount which is 3–5 times the amount of maneb. For this purpose it would be extra advantageous to use a maneb dispersion made up in an oily component as described above.

It is important that the oily component is deposited as a protecting membrane round the green parts of the potato plant. In order to avoid washing off and to avoid that the relatively high content of oil will act phytotoxically on the potato plant it is important that the content of surfactant is as low as possible. On the other hand, the products must be storage-stable, and it should still be possible to mix the composition with water in order to prepare the spraying liquid.

An interesting aspect of the invention is a pesticidal composition comprising a dithiocarbamate such as maneb in an amount of 1–55, preferably 5–50% by weight, more preferably 10–40% by weight, especially 15–35% by weight, suspended in an oily component which is used in an amount of 20–90% by weight, preferably 33–80% by weight, more preferably 40–75% by weight, and especially 45–70% by weight, and comprising a surfactant component in an amount of 1–45% by weight, preferably 2–30% by weight, more preferably 3–25% by weight, most preferably 4–20% by weight and especially 5–12% by weight. The surfactant component may comprise a stabilizing constituent comprising a $C_{5-30}$ hydrocarbyl or hydrocarbylene chain carrying a group capable of forming hydrogen bonds with water, and optionally one or more other constituents selected from the group consisting of non-ionic and ionic surfactants, the stabilizing constituent being present in an amount of at least 4% by weight, calculated on the total amount of surfactant component in the composition. The group capable of forming hydrogen bonds is as defined above. Especially, in the maneb composition described above, the surfactant component may comprise one or more ionic surfactant constiuent(s) and optionally one or more non-ionic surfactant constituent(s) as defined above, the ionic surfactant constituent comprising at least one amino group-containing surfactant which is present in an amount of at least 4% by weight, calculated on the total amount of surfactants. The amino group-containing surfactant is as defined above.

The particle size of maneb is important; it is most advantageous that at least 50% by weight have a particle size of less than 20$\mu$, preferably less than 10$\mu$, and more preferably less than 5$\mu$, in the compositions in which the maneb is suspended in the oily component.

Another interesting composition according to the invention is a fungicidal concentrate composition containing a dithiocarbamate such as maneb in suspended form, the amount of dithiocarbamate is 1–55%, preferably 5–50%, more preferably 10–40%, and especially 15–35% by weight of the total composition, e.g. 20% maneb, suspended in a mineral oil, especially a mineral oil having a content of aromatics less than 10% in an amount of 20–90%, preferably 33–80%, more preferably 40–75% and most preferably 45–70%, e.g. about 72%, calculated on the weight of the total composition, a non-ionic surfactant containing one or more ethoxylated, propoxylated or co-ethoxylated/propoxylated fatty alcohols; ethoxylated, propoxylated or co-ethoxylated/propoxylated mono-, di- or trialkylated phenols, which e.g. comprises 3–10 oxyethylene units, and in which the alkyl group comprises 6–20 carbon atoms (for the fatty alcohol) or 4–15 carbon atoms (for the alkylated phenols), especially 6–12 carbon atoms, and/or optionally an ethoxylated dialkyl phenol, which may e.g. comprise 4–14 oxyethylene units and in which the alkyl groups comprise 4–15, preferably 6–12 carbon atoms, in which the surfactant component comprises at least one $C_{5-30}$-alkyl amine which is ethoxylated, propoxylated or co-ethoxylated/propoyxlated, and in which the alkyl group preferably comprises 8–22 carbon atoms, and the oxyalkylene chain is preferably a polyoxyethylene chain with 3–25, preferably 6–20 oxyethylene units, e.g. a coco alkylamine with 10 oxyethylene units, and in which the surfactant component comprises at least one amino group-containing surfactant with at least one $C_{5-30}$-hydrocarbyl or hydrocarbylene chain, preferably with 7–22, and especially with 9–18 carbon atoms, carrying at least one carboxy group and/or sulphonic acid group, e.g. coco alkyl-$\beta$-amino propionic acid, and in which the total amount of surfactant component constitutes 1–45%, preferably 2–30%, more preferably 3–25%, most preferably 4–20% and especially 5–12%, e.g. 5.5% by weight of the total composition, and the amino group-containing surfactant constitutes at least 4%, preferably 8–60%, more preferably 12–45% and especially 18–35%, e.g. 29%, by weight of the total amount of surfactant. The composition may further comprise fillers, e.g. bentone in an amount of 0.3% by weight.

When the pesticidal concentrate compositions according to the invention are diluted with water in order to make ready-to-use spray liquids to be sprayed on the crop fields an aqueous oil-in-water emulsion in which the oily phase constitutes 0.1–10%, preferably 0.2–6%, more preferably 0.5–4% and especially 1–2.5%, by weight is formed, the oily phase containing pesticide suspended therein, and a surfactant component, and optionally inorganic filler material, the surfactant component comprising one or more stabilizing constituents comprising a $C_{5-30}$ hydrocarbyl or hydrocarbylene chain carrying a group capable of forming hydrogen bonds with water, and optionally one or more constituents selected from the group consisting of non-ionic and ionic surfactants, the stabilizing constituent being present in an amount of at least 4% by weight, calculated on the total amount of surfactant component in the composition, and the amount of water constituting 90–99,9% by volume, calculated on the oil-in-water emulsion. A $C_{5-30}$-hydrocarbyl or hydrocarbylene chain carrying a group capable of forming hydrogen bonds with water is as defined above. As a group capable of forming hydrogen bonds with water, amino and hydroxy groups may be mentioned. The amount of water in the pesticidal compositions ready to be used constitutes preferably 94–99.8%, more preferably 96–99.5%, and most preferably 97.5–99%, by volume.

Especially preferred surfactants components in aqueous spray liquids in oil-in-water emulsion from comprising one or more pesticides in suspended form are surfactants in which the nitrogen-containing ionic surfactant does not at the same time comprise a phosphate ester group.

Some oily component-comprising suspensions tend to separate and the viscosity tends to increase so that the total composition is a greasy, incoherent mass. In such cases, the suspension may be rendered homogeneous and easy-running by addition of a certain amount of a non-volatile mono-, di- or polychlorinated hydrocarbon or a non-volatile fatty alcohol such as nonanol or decanol, the amount of added hydrocarbon or alcohol being 0.2–20% by weight, preferably 1–10% by weight, especially 2–6% by weight, based on the total concentrate composition. This fatty alcohol being a part of the surfactant component and being present in an amount of at least 4% by weight of the total amount of surfactant in the composition, preferbly 6–60%, more preferably 8–45%, and especially 12–35%, by weight, calculated on the total amount of surfactant component in the composition. This tendency is especially important when the oily component is mineral oil and the pesticide is a relatively impure compound such as a technical grade of chloridazon (normal purity 80–85%). The addition of the fatty alcohol will furthermore increase the wetting activity of the composition and, hence, such compositions will have an increasing tendency to be more evenly distributed on the surface of the leaves which again will improve the biological effect of the pesticidal composition. This beneficial effect seems to be generally applicable, and the mixture of mineral oil and alcohol and/or chlorinated hydrocarbon will be suitable, also when other surfactants than the amino group-containing surfactants are used.

The use of fatty alcohols in suspensions is based on an oily component is especially advantageous in compositions in which the content of surfactant component is high. The fatty alcohol reduces viscosity, increases the rate of mixing in water and stabilizes the storage stability. Herbicidal compositions comprising anionic surfactants, especially phosphate esters, may be improved with respect to the emulsification and dispersability characteristics in water by addition of fatty alcohols.

As an example of a herbicidal composition which will be decisively improved by means of fatty alcohol and an anionic surfactant may be mentioned a herbicidal composition for use in beet fields comprising 1–55% of suspended phenmedipham and/or desmedipham, preferably 5–50%, more preferably 10–40% and most preferably 15–35%, by weight of the total composition, or 1–55% of suspended chloridazon, preferably 5–50%, more preferably 10–40% and most preferably 15–35%, by weight, calculated on the total composition or a mixture of these in the amounts mentioned, e.g. 8% phenmedipham and/or 12% chloridazon suspended in an oily component which is not a fatty alcohol, e.g. a mineral oil (having a content of aromatics of less than 25%) in an amount of 20–90%, preferably 33–80%, more preferably 40–75% and most preferably 45–70%, e.g. about 46% mineral oil with a low content of aromatics and with a viscocity of 20 cSt at 40° C., and a fatty alcohol in an amount of 0.2–20%, preferably 1–10% and most preferably 2–6%, all percentages being calculated on the weight of the total composition, a non-ionic and ionic surfactant wherein the non-ionic member can be selected from the group consisting of block polymers, which are condensates of polyoxyethylene and polypropylene; ethoxylated, propoxylated or co-ethoxylated/propoxylated fatty alcohols; ethoxylated, propoxylated or co-ethoxylated/propoxylated mono-, di-, or trialkyl phenols, which e.g. comprises 3-14 oxyethylene units, and in which the alkyl group comprises 6-20 or 4-15, especially 6-12 carbon atoms; and mono-, di- or poly(carboxyl) fatty acid esters in which the alcohol moiety is selected from the group consisting of polyoxyethylene alcohols, polyoxypropylene alcohols, polyoxyalkylene alcohols composed of different glycols, polyalcohols and ethoxylated, propoxylated or coethoxylated propoxylated polyalcohols, and wherein the total amount of surfactant component constitutes 1-45%, preferably 2-40%, more preferably 5-30%, most preferably 10-25%, by weight of the total composition, this fatty alcohol being a part of the surfactant component and being present in an amount of at least 4% by weight of the total amount of surfactant in the composition, preferably 6-60%, more preferably 8-45%, and especially 12-35%, by weight, calculated on the total amount of surfactant component in the composition. The mixture may optionally comprise water and/or an filler for the purpose of stabilization.

When the compositions comprising phenmedipham and/or desmedipham and/or chloridazon suspended in the oily component and further comprising a fatty alcohol as a part of the surfactant component which also comprises at least one ionic and at least one non-ionic surfactant are used in the preparation of ready-to-use spray liquids to be sprayed on the crop fields, they are made up to aqueous liquids in which the above-mentioned solid pesticides are suspended and the oily component is emulsified by means of the surfactant mixture as defined above. In the ready-to-use spray liquids the amount of water constitutes 90-99.9% by volume, e.g. 94-99.8%, preferably 96-99.5%, more preferably 97.5-99%, by volume.

Especially preferred ionic surfactants to be used in the above-mentioned combination of ionic and non-ionic surfactants are anionic surfactants.

The anionic surfactant should preferably be present in acidic form as a partially neutralized salt. The pH should preferably be 2-4, especially about 3. The mixture may contain water, preferably in and amount of 0.1-20%, especially 1-10%. Additionally, an inorganic filler may be added.

As oily components may be used the types described hereinbefore.

The anionic surfactant is preferably an acidic phosphate ester. Preferred phosphate esters are mono- and diesters of ethoxylated, propoxylated and/or co-ethoxylated/propoxylated fatty alcohols, mono-, di- or trialkyl phenols or mono-, di- or tristyryl phenols; and esters of $C_4$-$C_{18}$ alkylalcohol which are not ethoxylated.

The anionic surfactant may be an alkyl sulphonic acid, an aryl sulphonic acid, an arylalkyl sulphonic acid or an alkylaryl sulphonic acid, such as, e.g., dodecylbenzene sulphonic acid. Another example of anionic surfactants is a phosphonic acid.

The fatty alcohol should contain a hydrocarbyl or hydrocarbylene group containing 4-30, preferably 7-22, especially 9-18, e.g. 10, carbon atoms. The number of hydroxyl groups must be 1-2, preferably 1. Particularly useful is a decanol, preferably n-decanol.

The anionic surfactants will often be most suitable as partially neutralized salts. Suitable salts are alkaline metal salts such as sodium and potassium salts, earth alkaline metal salts such as calcium and magnesium salts; ammonium salts, amine salts and especially alkanolamine salts, at the pH values stated above.

The particles of the phenmedipham and/or desmedipham and/or chloridazon are preferably used in finely ground form which means that at least 50% by weight of the pesticide particles have a particle size of less than 20μ, preferably less than 10μ, and more preferably less than 5μ. Grinding may be performed as described above.

When the surfactant component comprises a fatty alcohol constituent, it has been found that irrespective of whether the ionic surfactant constituent is anionic or cationic, it is a definite advantage if the non-ionic surfactant member of the surfactant component partly consists of a co-ethoxylated/propoxylated surfactant member. The co-ethoxylated/propoxylated surfactant member should preferably constitute 0.5-20%, more preferably 1-10%, most preferably 1.5-7%, especially 2-4%, by weight of the total composition. If the surfactant component does not contain a fatty alcohol it will still, but not to quite the same degree, be an advantage if the non-ionic surfactant member partly consists of a co-ethoxylated/propoxylated surfactant member. The co-ethoxylated/propoxylated surfactant member should preferably constitute 0.5-20%, more preferably 1-10%, most preferably 1.5-7%, especially 2-4%, by weight of the total composition.

Glyphosate ((N-phosphonomethyl)glycine) is a widely used non-selective herbicidal agent. It is highly effective against grasses and broad-leaved weeds. It is normally provided as an isopropyl amine salt with a content of 360 g/l of glyphosate. It is well-known that addition of surfactants can increase the biological effect, and commercially available products comprise surfactant.

A general problem when spraying glyphosate is that the uptake is time-dependent. Since the salt is highly soluble in water it is important that it does not rain for 4-6 hours after the spraying. This is especially a problem because a substantial part of weed control takes place in the autumn with potential high rainfall and when it is difficult to forecast the weather.

However, Applicants have found that this problem can be minimized by preparing compositions in which glyphosate in solid form is suspended in an oily component, the adhesive capacity of such products on drying on the plants being significantly greater than the adhesive capacity of conventional formulations in which the glyphosate is present as a dissolved salt.

This is surprising because glyphosate in water at 20° C. has a solubility of 12 g/l. Oil-containing suspension concentrates having a content of 25-40% of suspended finely ground, solid glyphosate must be sprayed on the fields in the form of aqueous dilution containing 1-2% of the concentrate composition so that the diluting water can dissolve the total amount of glyphosate, whereby it is in dissolved free form at the time when it is applied to the plants.

It has also been found that glyphosate, even if present as free glyphosate, has a surprisingly high biological effect.

In order that the glyphosate can be present in a non-salted (free) form presented as a slurry in water, it must have a pH below 4, preferably below 3.5 and more preferably below 3.

Relevant compositions which contain glyphosates and which can resist some influence of rain will be based on suspended solid finely ground glyphosate in a non-salted form in an amount of 1-55%, preferably 5-50%, more preferably 10-40%, and especially 15-35%, by weight of the total composition, suspended in an oil-containing component, e.g. a mineral oil-containing component. The mineral oil should preferably have an aromatic content of below 25%, especially below 10% by weight. The oil-containing composition may constitute 10-90%, 20-90%, preferably 33-80%, more preferably 40-75% and especially 45-70%, e.g. about 50%, all percentages being calculated by weight of the total composition. Furthermore, the glyphosate suspension should contain a surfactant component in an amount of 1-50%, preferably 2-40%, more preferably 5-30%, and most preferably 10-25%, by weight of the total composition. The final mixture may additionally contain water and/or filler.

It is not absolutely necessary that the glyphosate is in free, non-salted form. The glyphosate may be used in a solid, finely ground form and in wholly or partially salted form. It is necessary that the glyphosate is very slightly soluble in the oily component. If the solubility was too high in the oily component, the pesticidal composition will be physically unstable on storage. The solubility in the oily component, therefore, preferably be less than 2%, more preferably less than 1%, most preferably less than 0.5% and especially less than 0.1%, by weight. (In Danish patent application No. 4118/86 it is described that the sulphuric acid salt of glyphosate is at least as biologically active as the propylamine salt). Possible salts of glyphosate are salts with bases and strong acids. Examples of salts are salts with HCl, sodium, potassium and especially ammonium. When glyphosate is in wholly or partially salt form, pH will be in the range of 1-6, preferably 3-5.

A further aspect of the present invention relates to pesticidal concentrate compositions comprising 1-55% by weight of finely ground glyphosate in solid form suspended in 10-90% by weight of an oily component and 1-50% by weight of a surfactant component, calculated on the total composition. In a further aspect of the invention relating to glyphosate suspended in oily components, the surfactant component is composed in such a manner that the surface tension of the aqueous, ready-to-use-spray liquid is decreased so that good wetting characteristics are achieved (compared to the traditional, commercially available glyphosate formulation marketed under the name Roundup TM). Preferred compositions comprising glyphosate suspended in an oily component have after thinning in a ratio of 1% by weight concentrate composition to 99% by weight water a surface tension of about 30 mN/m. The commercially available Roundup TM diluted to the same concentration has a surface tension of about 40 mN/m.

The disadvantages of aqueous salt solutions such as Roundup TM are i.a. that the amount and the surface tension decreasing effect of the added surfactant depend on the salt concentration. That means that an increased concentration of glyphosate decreased the amount of surfactants and the efficiency (less wetting) caused by the surfactants. The same does not apply to suspensions prepared in oily components because the glyphosate is not present in dissolved form which means that there is no risk that the surfactant can be salted out by the high content of glyphosate used. It is surprising that glyphosate is especially well suited for a formulation in the form of a finely ground substance in an oily component in which the content of the dispersed glyphosate is especially high, e.g. 40-50% by weight, calculated on the total composition. Hence, it is possible to prepare glyphosate compositions comprising glyphosate dispersed in an oily component, the composition comprising 40-50% glyphosate; when such compositions are diluted with water of 1% by weight of the composition and 99% by weight of water, the surface tension of the diluted liquid is about 30 mN/m.

Especially suitable oil-containing suspension compositions containing glyphosate will be those wherein at least 50% by weight of the solid particles are smaller than $20\mu$, preferably smaller than $10\mu$ and more preferably smaller than $5\mu$. The grinding process may be performed as described above.

An important feature of said glyphosate composition is that the pH in dilutions with limited amounts of water, e.g. composition/water in the ratio 1/1, is below 4, preferably below 3.5, and more preferably below 3, and especially below 2.5, e.g. 2.

When the glyphosate compositions in which glyphosate is suspended in an oily component are diluted to form ready-to-use spray liquids to be sprayed on the fields the aqueous liquid will comprise glyphosate and an emulsified oily substance and a surfactant. The glyphosate will either be in a partly solid dispersed form and in a partly dissolved form or in a totally dissolved form. The state of the glyphosate will especially be dependent on the amount of water used in the dilution. Furthermore, it is characteristic of the aqueous dilution that the pH is below 4, preferably below 3.5, and more preferably below 3, and especially below 2.5, e.g. 2. In the aqueous liquid comprising suspended glyphosate and an emulsified oily substance and further comprising a surfactant composition to be used as a spray liquid in the agriculture, the amount of water constitutes 90-99.9% by volume, e.g. 94-99.8%, preferably 96-99.5%, more preferably 98.5-99%, by volume.

The oily substance in the glyphosate compositions is as described in connection with other pesticidal compositions according to the present invention.

It has been found that if 0.2-20%, preferably 1-10%, and more preferably 2-6%, by weight of the total composition are constituted by a fatty alcohol, the presence of the fatty alcohol can give a physical stabilization of the total composition when stored. This fatty alcohol being a part of the surfactant component and being present in an amount of at least 4% by weight of the total amount of surfactant in the composition, preferably 6-60%, more preferably 8-45%, and especially 12-35%, by weight, calculated on the total amount of surfactant component in the composition. Furthermore, the fatty alcohol content can improve the emulsion stability in water and increase the distribution of the composition on the sprayed crops, which is an advantage with respect to the biological effect.

Especially preferred fatty alcohols are those wherein a hydrocarbyl or hydrocarbylene group contains 5-30, preferably 7-22, and more preferably 9-18, e.g. 10, carbon atoms. The number of hydroxy groups should be 1-2, preferably 1. Particularly suitable is decanol, preferably n-decanol.

Preferred surfactant constituents for compositions in which glyphosate is suspended in an oily component, or aqueous mixtures containing glyphosate in an oily component and an surfactant constituent will be compositions containing both a ionic surfactant and a non-ionic surfactant member.

Preferred non-ionic surfactant members are members selected from the group consisting of block polymers, which are condensates of polyoxyethylene and polypropylene; ethoxylated, propoxylated or co-ethoxylated/propoxylated fatty alcohols; ethoxylated, propoxylated or co-ethoxylated/propoxylated mono-, di- or trialkyl phenols, which, e.g., comprises 3-14 oxyethylene units, and in which the alkyl group comprises 6-20 carbon atoms (for fatty alcohol) or 4-15 carbon atoms (for alkylated phenols), especially 6-12, carbon atoms; and mono-, di- or poly(carboxyl) fatty acid esters in which the alcohol moiety is selected from the group consisting of polyoxyethylene alcohol, polyoxypropylene alcohol, polyoxyalkylene alcohols combined from different glycols, polyalcohols, and ethoxylated, propoxylated and co-ethoxylated/propoxylated polyalcohols.

Preferred ionic surfactant constituents to be used in compositions which contain glyphosate suspended in an oily component, or aqueous mixtures containing glyphosate, an oily component and a surfactant component, are especially those wherein the composition contains at least one amino group-containing surfactant. Especially preferred ionic surfactants contain at least two different amino group-containing members, which in addition to the hydrocarbyl or hydrocarbylene chain carries groups of different functionality. The most advantageous ionic amino group-containing members are those which do not additionally contain a phosphate ester group. Reference is made to the above description of the ionic amino group-containing surfactants and the ionic compositions containing them. Especially suitable compositions will be those wherein a strong organic acid or mineral acid has been added to the composition.

The use of ionic amino group-containing surfactant constituents for compositions with glyphosate suspended in an oily component caused the suspensions to become particularly storage-stable with a limited tendency to sediment during storage without the use or with only limited use of inorganic filler.

Other useful ionic surfactant constituents are anionic surfactants. Particularly useful anionic surfactants are those wherein the anionic surfactant is an acidic phosphate ester. It has been found that phosphate esters in combination with fatty alcohols can form storage-stable suspensions with good stability properties and advantageous emulsifying and distributional properties on admixture with water.

Especially preferred phosphate esters are mono- and diesters of ethoxylated, propoxylated and/or co-ethoxylated fatty alcohols, mono-, di- or trialkyl phenols or mono-, di- or tristyryl phenols; or esters of non-ethoxylated $C_4$-$C_{18}$ alkyl alcohols.

Furthermore, the anionic surfactant may be an alkyl sulphonic acid, an aryl sulphonic acid, an aralkyl sulphonic acid or an alkylaryl sulphonic acid, such as, e.g. dodecylbenzene sulphonic acid. The anionic surfactant may also be a phosphonic acid.

The anionic surfactants will often be most suitable as partially neutralized salts. Useful salts are alkaline metal salts such as sodium and potassium salts, earth alkaline metal salts such as calcium and magnesium salts, ammonium salts, amine salts and alkanol amine salts, at the pH values stated above.

The above-described method for preparing oil-based compositions may be used in the preparation of all diluted compositions comprising pesticides.

When the pesticide is a herbicide such as phenmedipham or desmedipham, an amount of about 1 kg/ha is used each season. When the pesticide is a herbicide such as metamitron, an amount of about 3-4 kg/ha is used each season. When a mixture of phenmedipham and metamitron is used, an amount of 0.5 kg/ha of phenmedipham is used each season and an amount of about 2 kg/ha of metamitron is used each season. When the pesticide is a herbicide such as chloridazon, an amount of about 2 kg/ha is used each season. When the pesticide is a herbicide such as glyphosate, an amount of 1-2 kg/ha is used each season. The amounts stated can be divided in 2 or more doses.

Thus, compositions comprising both the phenmedipham (or desmedipham) and components selected from chloridazon and metamitron are advantageous in that the content of active ingredient may be kept at a lower level as phenmedipham or desmedipham is more active per weight unit than the other herbicidally active components mentioned above.

The above-mentioned compound metamitron is used as a herbicide for beets. When metamitron in some cases is preferred instead of phenmedipham (or desmedipham) which is used in a dosis of about 1 kg/ha only, this is due to the fact that metamitron has a better biological effect against cleavers goose grass (*Galium aparine*), nippelwort (*Lapsana communis*) and black nightshade (*Solanum nigrum*). A much better biological effect is obtained in the combating of corn marigold (*Chrysanthemum segetum*), wild chamomile (*Matricaria chamomilla*), small nettle (*Urtica urens*) and anual meadow grass (*Poa annua*). The other 15-20 weed species in beets which are common in Denmark are combated equally well with phenmedipham and metamitron.

When the pesticide is a fungicide such as maneb, which is mainly used for controlling fungi on potatoes, an amount of 3-4 kg/ha is used for each spray which is repeated several times during the growth season, e.g. 3-4 times. The oil in the composition forms a protecting layer on the leaves which protects the plant against attack by lice. Hence, the fungicidal composition also exerts an insecticidal effect.

Some ingredients used in the examples are marked with 1)-19). They are commercially available products supplied from the following manufacturers:
1) Solvent refined paraffinic oil (Norsk Hydro) (aromatics 4%, viscosity 19.7 cSt at 40° C.)
2) Paraffinic hydrocarbon, <0.1% of aromatic hydrocarbon, boiling point 190°-240° C., flash point >70° C. (Haltermann)
3) Ethoxylated nonylphenol (4 oxyethylene units per molecule) (Berol Kemi)
4) Ethoxylated dinonylphenol (9 oxyethylene units per molecule) (Berol Kemi)
5) Acidic phosphoric acid ester (Berol Kemi)
6) 70% solution of cocoalkyl β-amino-propionic acid in an alcohol mixture (Kenogard)
7) Attapulgite clay, colloidal grades (Chemie-Mineralien G.M.B.H.)
8) Ethoxylated cocoalkylamine (10 oxyethylene units per molecule) (Hoechst)
9) Solvent refined paraffinic oil (Shell) (aromatics 5%, naphtenics 33%, paraffinics 62%, viscosity 27 cSt at 40° C.)

10) Organic derivate of hectorite clay (NL Chemicals)
11) n-Decanol (Aarhus Oliefabrik A/S)
12) Co-ethoxylated/propoxylated fatty alcohol (Hoechst)
13) 64% Sodium-oleyl-N-methyl tauride (Hoechst)
14) Approx. 99% aromatic solvent, b.p. 190°–210° C., flash point 66° C., (Esso)
15) Ethoxylated dinonyl phenol (16 oxyethylene units per molecule) (Berol Kemi)
16) Co-ethoxylated/propoxylated alkyl phenol (about 80%) (Berol Kemi)
17) Acidic phosphoric ester of ethoxylated alkyl phenol (GAF)
18) Co-ethoxylated/propoxylated fatty alcohol having a terminal methylated OH group (Rewo Chemical Group)
19) Ethoxylated castor oil (36 oxyethylene units per molecule) (Hoechst)
20) Refined 50% parafinic mineral oil, aromatic 17%, viscosity 20 cSt at 40° C. (Shell)
21) Technical grade of 2-ethyl hexyl stearate, comprises about ⅔2-ethyl hexyl stearate and about ⅓ ethyl hexyl palmitate (Oleofina)

EXAMPLE 1

Metamitron and phenmedipham suspensions in an oily anhydrous component. Comparison between prior art compositions and a composition according to the invention Test samples with the contents illustrated in Table 1 were prepared by mixing the oily components and surfactants. The surfactants and oily components together constitute 75% of the resulting mixture in sample 1a and approx. 67% in samples 1b and 1c. The components were mixed thoroughly, and the pH modifiers were added. Subsequently, 19.4% or 26.8% metamitron (98% technical grade), respectively, and 6.7% or 6.2% phenmedipham (97% technical grade), respectively, was stirred in. Subsequently to the mixing process a wet grinding on a "Mini" Mill was performed, so that a total of 200 g test sample was ground for 10 minutes. (A "Mini" Mill is a Motormill manufactured by Eiger Engineering LTD Warrington, Chesire, England, Model M 50 VSE TVF and loaded with about 35 ml of zirconia beads, size 1 mm).

All the test samples were ground to a homogeneous liquid paste (the suspension).

Dilution testing was performed by adding 3 ml of the suspension prepared as described above to 100 ml of water in a 150 ml beaker. Sample 1a emulsified most easily and sample 1b emulsified worst. The mixture of water and suspension was stirred thoroughly with a magnetic stirrer for 30 minutes. In sample 1b, an oil precipitation took place. In sample 1a, the oil precipitation was smaller. Despite the fact that the content of surfactant was smallest in sample 1c, sample 1c was the only sample in which oil and pesticide did not form greasy precipitates. In sample 1 b, the precipitation was extremely pronounced while more limited for sample 1a. It should be added, that in all three tests, effort was made to optimize the emulsifier mixture.

Sample 1a is identical with a mixture of samples "I" and "II" as disclosed in Example 18 of European patent application published under no. A2.142670 in the recommended mixture ratio. Sample 1b corresponds to 1a but contains an additional amount of metamitron. Sample 1c was the composition according to the present invention.

It was evident that the oil-containing pesticide suspension in which the ionic surfactant is an ampholyte is the most preferred one as there is no oily precipitation after dilution with water.

TABLE 1

|  | Amounts, % by weight | | |
|---|---|---|---|
|  | 1a | 1b | 1c |
| Sample Ingredients | | | |
| Oily components | | | |
| Hydropara 19[1] | 50.5 | 42.3 | 45.5 |
| Halpasol TM 190/240[2] | 10.0 | 14.0 | 14.0 |
| Surfactant constituents | | | |
| Berol TM 26[3] (non-ionic) | 3.1 | 2.4 | 2.4 |
| Berol TM 269[4] (non-ionic) | 5.0 | 4.0 | 3.0 |
| Berol TM 724[5] (anionic) | 4.3 | 3.6 | — |
| Ampholyte SKKP-70[6] (ampholytical, amino group-containing) | — | — | 1.8 |
| % amino group-containing surfactant of total surfactant component | — | — | 18.9 |
| pH modifiers | | | |
| Monoethanolamine | 1.0 | 0.7 | — |
| Maleic acid anhydride | — | — | 0.3 |
| Pesticide components | | | |
| Metamitron, 98%, | | | |
| in ground state*, | 19.4 | 26.8 | 26.8 |
| ~pure metamitron | 19 | 26.2 | 26.2 |
| Phenmedipham, 97%, | | | |
| in ground state*, | 6.7 | 6.2 | 6.2 |
| ~pure phenmedipham | 6.5 | 6.0 | 6.0 |
| Assay | | | |
| Precipitation tendency after 30 min. stirring of 3% composition in water | minimum | pronounced | none |

*Particle size: more than 50% by weight was smaller than 5μ.

EXAMPLE 2

Metamitron and Phenmedipham suspensions in the oily component

Test samples with the contents illustrated in Table 2 were mixed and ground in the same manner as described in Example 1 above. In each of the four samples shown, the content of solids constituted 35% and the liquid constituted 65%.

Estimation of the ease of dilution with water and the forming of a ready-to-use spray liquid was made by filling 100 ml of water into a 150 ml beaker and transferring 3 ml test sample weighed out into the beaker. In each beaker, a glass spatula was moved forwards and backwards in the water. The amount of residuary preparation not yet dispersed in the water phase and observable as small lumps of gel floating on the surface of the liquid was estimated by visual observation. It was evident that samples 2a and 2b were not miscible with the water phase in the same way as samples 2c and 2d. This means that the samples with no ethoxylated amine were only slightly dispersable in the water diluent. After 5 min. stirring with a magnetic stirrer, sample 2a was considerably better dispersed than sample 2b. The composition of the surfactant was identical in samples 2a and 2b, but the amounts used were different. Hence, it was the large amount present in sample 2b which retarded the rate of dissolution. Presumably, a gel formation took place between surfactant and water. The ethoxylated amine did not provide a better emulsion stability, but served the mere purpose of ensuring a rate of dissolution for suitable practical use.

TABLE 2

| | Amounts, % by weight | | | |
|---|---|---|---|---|
| | 2a | 2b | 2c | 2d |
| Sample Ingredients | | | | |
| Oily component | | | | |
| Hydropara 19[1] | 46.8 | 44.2 | 47.15 | 42.5 |
| Halpasol TM 190/240[2] | 10 | 10 | 10 | 10 |
| Surfactant constituent | | | | |
| Berol TM 26[3] (non-ionic) | 2.4 | 3.2 | 2.4 | 3.8 |
| Berol TM 269[4] (non-ionic) | 3 | 4 | 2.5 | 4 |
| Genamin TM C-100[8] (cationic, amino group-containing) | | | 0.6 | 1 |
| Ampholyte SKKP-70[6] (ampholytical, amino group-containing) | 1.8 | 2.4 | 1.5 | 2.4 |
| Total surfactant | 6.66 | 8.88 | 6.55 | 10.48 |
| % amino-group-containing surfactant of total surfactant composition | 19 | 19 | 25.4 | 25.6 |
| pH modifier Perchloric acid 70% | 1.0 | 1.2 | 0.85 | 1.3 |
| Inorganic filler Attagel TM 40[7] | 2 | 2 | 2 | 2 |
| Pesticide | | | | |
| Metamitron, 98%, | | | | |
| finely ground*, | 26.8 | 26.8 | 26.8 | 26.8 |
| ~pure metamitron | 26.2 | 26.2 | 26.2 | 26.2 |
| Phenmedipham, 97%, | | | | |
| finely ground*, | 6.2 | 6.2 | 6.2 | 6.2 |
| ~pure phenmedipham | 6.0 | 6.0 | 6.0 | 6.0 |
| Assay | | | | |
| Tendency of gel formation after dilution with water | strong | strong | minimum | minimum |
| Diluted after 5 min. stirring with a magnetic stirrer | yes | no | yes | yes |

*Particle size: more than 50% by weight was smaller than 5μ.

EXAMPLE 3

Metamitron and phenmedipham suspensions in the oily component stabilized with varying amounts of strong acid Samples with the composition illustrated in Table 3 were mixed and ground in the same way as described in Example 1 above.

The test samples were stored for a period of two months at 25° C. and 50° C., respectively, and they were shaken prior to analysis. Both of the active substances were analysed by the HPLC-method. It is evident from the results that the nature of the acid, the amount of acid and the pH-value influenced the storage stability of the phenmedipham.

TABLE 3

| | Amounts, % by weight | | | |
|---|---|---|---|---|
| | 3a | 3b | 3c | 3d |
| Sample Ingredients | | | | |
| Oily component | | | | |
| Hydropara 19[1] | 45.3 | 45.1 | 45 | 44.6 |
| Halpasol TM 190/240[2] | 10 | 10 | 10 | 10 |
| Surfactant constituent | | | | |
| Berol TM 26[3] (non-ionic) | 2.4 | 2.4 | 2.4 | 2.4 |
| Berol TM 269[4] (non-ionic) | 3 | 3 | 3 | 3 |
| Genamin TM C-100[8] (cationic, amino group-containing) | 1 | 1 | 1 | 1 |
| Ampholyte SKKP-70[6] (ampholytical, amino group-containing) | 1.8 | 1.8 | 1.8 | 1.8 |

TABLE 3-continued

| | Amounts, % by weight | | | |
|---|---|---|---|---|
| | 3a | 3b | 3c | 3d |
| pH modifier | | | | |
| Maleic acid anhydride | — | 0.2 | 0.3 | — |
| Perchloric acid, 70% | — | — | — | 0.7 |
| Inorganic filler Attagel TM 40[7] | 2 | 2 | 2 | 2 |
| Pesticide component | | | | |
| Metamitron, 98% | 28 | 28 | 28 | 28 |
| Phenmedipham, 97% | 6.5 | 6.5 | 6.5 | 6.5 |
| Assay | | | | |
| pH, 10% in demineralized water | 5.7 | 4.8 | 3.8 | 2.9 |
| Analysis, Metamitron | | | | |
| Start | 27.2 | 27.5 | 26.3 | 28.1 |
| After 60 days at 25° C. | 26.6 | 27.6 | 26.6 | 28.1 |
| After 60 days at 50° C. | 25.6 | 25.8 | 26.3 | 27.8 |
| Analysis, Phenmedipham | | | | |
| Start | 6.5 | 6.3 | 5.9 | 6.4 |
| After 60 days at 25° C. | 6.1 | 6.1 | 5.9 | 6.4 |
| After 60 days at 50° C. | 5.3 | 5.3 | 5.5 | 6.3 |

EXAMPLE 4

Compositions comprising metamitron and phenmedipham in an oily component and containing different amounts of inorganic fillers and optionally water Test samples with contents shown in Table 4 were prepared by mixing and grinding as described in Example 1. However, the content of attagel, water and propylene glycol was not added until after the grinding in the "Mini Mill". Hereby the attagel maintained its structure of long crystal needles. After the grinding the attagel was admixed with vigorous stirring in a high speed mixer.

In the examples the compositions had been improved by addition of minor amounts of co-ethoxylated/-propoxylated surfactant (Genapol TM 2909). Small amounts of Arkopon TM T (sodium-oleyl-methyl tauride) which, in the preparation, are reacted with an acid, enhanced the dispersing capacity and had a synergistic effect on the other nitrogen-containing ionic surfactants. It was observed that the increased content of attagel which had not been ground together with the other components resulted in a slower precipitation of the insoluble components in the samples for storing.

It was also found that the addition of small amounts of water (below 2%) may have a good effect on the storage stability without a too high increase of the solubility of the metamitron.

In comparison with the samples stated in Table 2 a reduction in the metamitron content, but an increase in the phenmedipham and attagel contents, had taken place. The compositions of Tables 2 and 4 must be used in the same dosages per hectare.

TABLE 4

| | Amounts, % by weight | | | |
|---|---|---|---|---|
| | 4a | 4b | 4c | 4d |
| Sample Ingredients | | | | |
| Oily component | | | | |
| Hydropara 19[1] | 45.5 | 44.5 | 44.5 | 44.5 |
| Halpasol TM 190/240[2] | 10 | 10 | 10 | 10 |
| Surfactant constituent | | | | |
| Berol TM 26[3] (non-ionic) | 2.6 | 2.6 | 2.6 | 2.6 |
| Berol TM 269[4] (non-ionic) | 2.4 | 2.4 | 2.4 | 2.4 |
| Genapol TM 2909[12] | 0.8 | 0.8 | 0.8 | 0.8 |
| Genamin TM C-100[8] (cationic, amino | 0.6 | 0.6 | 0.6 | 0.6 |

TABLE 4-continued

| | Amounts, % by weight | | | |
|---|---|---|---|---|
| | 4a | 4b | 4c | 4d |
| group-containing) | | | | |
| Ampholyte SKKP-70[6] | 1.9 | 1.9 | 1.9 | 1.9 |
| (ampholytical, amino group-containing) | | | | |
| Arkopon TM T Pulver hochkonz.[13] | 0.6 | 0.6 | 0.6 | 0.6 |
| (anionic) | | | | |
| Total surfactant | 8.1 | 8.1 | 8.1 | 8.1 |
| % amino group-containing surfactant of total surfactant composition | 23.8 | 23.8 | 23.8 | 23.8 |
| pH modifier | 1.1 | 1.1 | 1.1 | 1.1 |
| Perchloric acid 70% | | | | |
| Water | — | — | 1.0 | — |
| Propylene glycol | — | — | — | 1.0 |
| Inorganic filler | 3 | 4 | 3.0 | 3.0 |
| Attagel TM 40[7] | | | | |
| Pesticide | | | | |
| Metamitron, 98%, | | | | |
| finely ground*, | 24.8 | 24.8 | 24.8 | 24.8 |
| ~pure metamitron | 24.3 | 24.3 | 24.3 | 24.3 |
| Phenmedipham, 97%, | | | | |
| finely ground*, | 6.7 | 6.7 | 6.7 | 6.7 |
| ~pure phenmedipham | 6.5 | 6.5 | 6.5 | 6.5 |
| Assay | | | | |
| pH, 10% in demineralized water | 3.0 | 3.1 | 3.2 | 3.1 |
| Tendency to form a redispersable sediment in concentrate | | moderate | | |
| Tendency of gel formation after dilution with water | | minimum | | |
| Mixing rate in water | | satisfactory | | |

EXAMPLE 5

Phenmedipham compositions with a low content of water in the liquid phase

Test samples with contents illustrated in Table 5 were prepared by initially mixing the oily component, the surfactants, water and the acidic component. To this mixture, which constituted 77-81% of the resulting composition, 23-19% of phenmedipham (technical grade) and Attagel were added with stirring. The test samples were mixed and ground on a "Mini" Mill so that a total of 200 g test sample was ground for 8-10 min. All the test samples were ground to a homogeneous paste of moderate viscosity.

Phenmedipham is a herbicide which is used in small amounts (about 1 kg per hectare). Surfactant and mineral oil greatly promote the herbicidal effect of the phenmedipham. Thus, a high content of phenmedipham is not particularly desirable for suspension preparations containing only phenmedipham as the active ingredient since this may result in an amount of activating auxiliary substances below the optimal amount.

A low content of water and Attagel TM leads to a suspension with a low viscosity and thus a maximum tendency for the content of solid to sediment. A low content of surfactant has the same effect. On the other hand, a low viscosity provides the best distribution when diluting with water; however, when storing pure suspensions of phenmedipham the dispersability in water might be impaired when the content of surfactant is low. Such a tendency was demonstrated for sample 5a wherein the content of surfactant is just above 10%. The best physical properties were demonstrated for sample 5b. When testing the dispersability, 2 g of the composition were added to 100 ml of water.

TABLE 5

| | Amounts, % by weight | | | |
|---|---|---|---|---|
| | 5a | 5b | 5c | 5d |
| Sample Ingredients | | | | |
| Oily component Hydropara 19[1] | 64.5 | 59 | 53.5 | 55 |
| Surfactant constituent | | | | |
| Berol TM 26[3] (non-ionic) | 2.35 | 3.5 | 4.65 | 3.5 |
| Berol TM 269[4] (non-ionic) | 6.05 | 9.1 | 12.15 | 9.1 |
| Ampholyte SKKP-70[6] (ampholytical, amino group-containing) | 1.8 | 2.7 | 3.6 | 2.7 |
| Genamin TM C-100[8] (cationic, amino group-containing) | 1 | 1.5 | 2 | 1.5 |
| Total surfactant | 10.66 | 16 | 21.32 | 16 |
| % amino-group-containing surfactant of total surfactant composition | 21.2 | 21.2 | 21.2 | 21.2 |
| pH modifier | 0.8 | 1.2 | 1.6 | 1.2 |
| Perchloric acid 70% | | | | |
| Water | 4 | 4 | 3.5 | 4 |
| Inorganic filler Attagel TM 40[7] | 2 | 1.5 | 1.5 | 1 |
| Pesticide component | | | | |
| Phenmedipham, 97% | 17.5 | 17.5 | 17.5 | 22 |
| ~pure phenmedipham | 17 | 17 | 17 | 21.3 |
| Assay | | | | |
| pH (10% in water) | 3.8 | 3.4 | 3.2 | 3.2 |
| Tendency of oil-precipitation in concentrate under storage | strongest | moderate | moderate | moderate |
| Dispersability when stirring a freshly prepared composition into water | best | good | fair | fair |
| Dispersability when stirring a 7 days old composition into water | worst | good | fair | fair |

EXAMPLE 6

Compositions comprising phenmedipham suspended in an oily component in which a low content of water is incorporated Test samples with compositions illustrated in Table 6 were mixed and ground in the same way as described in Example 1 above.

It appears that the products comprising the fatty alcohol (n-decanol) yield the fastest dispersability when the compositions are diluted with water in the ratio of 3% of concentrate composition to 97% of water.

TABLE 6

| | Amounts, % by weight | | | |
|---|---|---|---|---|
| | 6a | 6b | 6c | 6d |
| Sample Ingredients | | | | |
| Oily component Hydropara 19[1] | 55.6 | 56.5 | 55.4 | 55.3 |
| Surfactant constituent | | | | |
| Hyfatol TM 10[11] (fatty alcohol) | — | — | 3.5 | 3.5 |
| Berol TM 26[3] (non-ionic) | 2 | 2 | — | — |
| Berol TM 269[4] (non-ionic) | 9 | 9 | 10 | 10 |
| Rewopal MT TM 2540[18] (non-ionic) | 2 | 2 | — | — |
| Berol TM 922 (non-ionic) | — | — | 2 | 2 |
| Genamin TM C-100[8] (cationic, amino group-containing) | 1.5 | 1.5 | 1.5 | 1.5 |
| Ampholyte SKKP-70[6] (ampholytical, amino | 2.7 | 2.7 | 3.2 | 3.2 |

TABLE 6-continued

|  | Amounts, % by weight | | | |
|---|---|---|---|---|
|  | 6a | 6b | 6c | 6d |
| group-containing) | | | | |
| Total surfactant | 16.4 | 16.4 | 19.2 | 19.2 |
| % amino-group-containing surfactant of total surfactant composition | 20.7 | 20.7 | 23.8 | 23.8 |
| % fatty alcohol of total surfactant composition | — | — | 18 | 18 |
| pH modifier | | | | |
| Perchloric acid 70% | 1.2 | 1.3 | 1.4 | 1.5 |
| Water | 4 | 4 | 4 | 4 |
| Inorganic filler | | | | |
| Attagel TM 40[7] | 1.5 | 1.5 | 1.5 | 1.5 |
| Pesticide component | | | | |
| Phenmedipham, 97% | 19.5 | 19.5 | 17.5 | 17.5 |
| ~pure phenmedipham | 18.9 | 18.9 | 17 | 17 |
| Assay | | | | |
| Dispersability when stirring into water | good | good | very good | very good |
| Emulsion stability in water | very good | very good | good | good |

EXAMPLE 7

Phenmedipham suspensions in a dispersion of tri-allate in the oily component

Test samples with compositions illustrated in Table 7 were prepared by initially mixing oil, surfactant and water. The tri-allate was stirred in followed by Attagel and phenmedipham, and the samples were mixed. Grinding was performed in the same manner as described in Example 1 above.

The emulsion stability of 3% suspension in water was assessed. It was found that the flocculation tendency is highly dependent on the amount of acidic component present. In the illustrated compositions the optimal amount is 1.15% of a 70% perchloric acid. When the content of perchloric acid is larger, the flocculation tendency increases.

TABLE 7

|  | 7a | 7b | 7c |
|---|---|---|---|
|  | Amounts, % by weight | | |
| Sample Ingredients | | | |
| Oily component | | | |
| Hydropara 19[1] | 50.55 | 50.45 | 50.35 |
| Surfactant constituent | | | |
| Berol TM 26[3] (non-ionic) | 4 | 4 | 4 |
| Berol TM 269[4] (non-ionic) | 7 | 7 | 7 |
| Genamin TM C-100[8] (cationic, amino group-containing) | 2.5 | 2.5 | 2.5 |
| Ampholyte SKKP-70[6] (ampholytical, amino group-containing) | 2.5 | 2.5 | 2.5 |
| Total surfactant | 15.2 | 15.2 | 15.2 |
| % amino group-containing surfactant of total surfactant composition | 28 | 28 | 28 |
| pH modifier | | | |
| Perchloric acid, 70% | 0.95 | 1.05 | 1.15 |
| Water | 2 | 2 | 2 |
| Inorganic filler | | | |
| Attagel TM 40[7] | 2 | 2 | 2 |
| Pesticide | | | |
| Phenmedipham, 97% ~ | 12.5 | 12.5 | 12.5 |
| pure phenmedipham | 12.1 | 12.1 | 12.1 |
| Tri-allate, 90% ~ | 16 | 16 | 16 |
| pure tri-allate | 14.4 | 14.4 | 14.4 |
| Assay | | | |
| pH (10% in demineralized water) | 4.0 | 3.7 | 3.5 |

TABLE 7-continued

|  | 7a | 7b | 7c |
|---|---|---|---|
|  | Amounts, % by weight | | |
| Flocculation tendency after dilution into water | biggest | limited | smallest |

EXAMPLE 8

Phenmedipham suspensions in a solution of tri-allate in the oily component

Test samples with compositions illustrated in Table 8 were prepared by initially mixing oily component, aromatic solvent, surfactant and optionally water. The tri-allate was stirred in followed by Attagel and phenmedipham, and the samples were mixed. Grinding was performed in the same manner as described in Example 1 above.

As all samples are of low viscosity they are easy to shake into uniform compositions even on standing for 6 months. After 6 months there is no tendency of forming a layer which cannot be distributed by slight shaking.

The addition of the solvent (Solvesso TM 150) for tri-allate increases the emulsification stability in water.

As the tri-allate is slightly unstable in the presence of water it would have been expected that a degradation of tri-allate had taken place on 6 months standing. However, analysis did not show a decrease in activity after 6 months.

TABLE 8

|  | 8a | 8b | 8c | 8d |
|---|---|---|---|---|
|  | Amounts, % by weight | | | |
| Sample Ingredients | | | | |
| Oily component | | | | |
| Hydropara 19[1] | 51.3 | 29.3 | 32.3 | 31.3 |
| Solvesso TM 150[14] | — | 20 | 20 | 20 |
| Surfactant constituent | | | | |
| Berol TM 26[3] (non-ionic) | 4 | — | — | — |
| Berol TM 269[4] (non-ionic) | 7 | 11 | 11 | 11 |
| Genamin TM C-100[8] (cationic, amino group-containing) | 2.5 | 2.5 | 2.5 | 2.5 |
| Ampholyte SKKP-70[6] (ampholytical, amino group-containing) | 2.5 | 2.5 | 2.5 | 2.5 |
| Total surfactant | 15.2 | 15.2 | 15.2 | 15.2 |
| % amino group-containing surfactant of total surfactant composition | 28 | 28 | 28 | 28 |
| pH modifier | | | | |
| Perchloric acid, 70% | 1.2 | 1.2 | 1.2 | 1.2 |
| Water | — | 2 | — | — |
| Inorganic filler | | | | |
| Attagel TM 40[7] | 3 | 3 | 2 | 3 |
| Pesticide component | | | | |
| Tri-allate, 90% ~ | 16 | 16 | 16 | 16 |
| pure tri-allate | 14.4 | 14.4 | 14.4 | 14.4 |
| Phenmedipham, 97% ~ | 12.5 | 12.5 | 12.5 | 12.5 |
| pure phenmedipham | 12.1 | 12.1 | 12.1 | 12.1 |
| Assay | | | | |
| pH (10% in demineralized water) start | 3.3 | 3.2 | 3.2 | 3.2 |
| pH (10% in demineralized water) after 6 months | 3.3 | 4.0 | 3.2 | 3.2 |
| Flocculation tendency after dispersion in water | some | none | none | none |
| Emulsion stability in water | fair | very good | good | good |

EXAMPLE 9

Chloridazon and phenmedipham suspensions in an oily component.

Samples of the composition illustrated in Table 9 (with the exclusion of Attagel TM) were mixed and ground in the same manner as described in Example 1 above. After the grinding process the Attagel TM was added.

It appears from the evaluation (estimation of precipitation in the concentrate on 4 months storage) that test samples 9b, 9c and 9d are more favourable than 9a, which is due to the addition of co-ethoxylated/propoxylated fatty alcohol in which the free hydroxy group is methylated (Rewopal MT TM 2540). The addition of the co-ethoxylated/propoxylated constituent yields a greatly improved emulsification stability on mixing with water.

The addition of 1% by weight of Attagel TM yields emulsions with excellent stability.

TABLE 9

| Sample Ingredients | 9a | 9b | 9c | 9d |
|---|---|---|---|---|
| | Amounts, % by weight | | | |
| Oily component | | | | |
| Hydropara 19[1] | 52.8 | 53.9 | 52.8 | 51.8 |
| Surfactant constituent | | | | |
| Berol TM 26[3] (non-ionic) | 2.5 | 0.5 | 0.5 | 0.5 |
| Berol TM 269[4] (non-ionic) | 9.5 | 11 | 11 | 11 |
| Rewopal MT TM 2540[18] (non-ionic) | — | 1.5 | 1.5 | 1.5 |
| Ampholyte SKKP-70[6] (ampholytical, amino group-containing) | 2.7 | 2.7 | 2.7 | 2.7 |
| Genamin TM C-100[8] (cationic, amino group-containing) | 1.5 | 1.5 | 1.5 | 1.5 |
| Total surfactant | 15.4 | 16.4 | 16.4 | 16.4 |
| % amino group-containing surfactant of total surfactant composition | 22 | 20.7 | 20.7 | 20.7 |
| pH modifier | | | | |
| Perchloric acid, 70% | 1.2 | 1.2 | 1.2 | 1.2 |
| Water | 9.0 | 7.0 | 7.0 | 7.0 |
| Inorganic filler | | | | |
| Attagel TM 40[7] | — | — | 1 | 2 |
| Pesticide component | | | | |
| Chloridazon, 97% ~ pure chloridazon | 12.5 / 12.1 | 12.5 / 12.1 | 12.5 / 12.1 | 12.5 / 12.1 |
| Phenmedipham, 97% ~ pure phenmedipham | 8.3 / 8.0 | 8.3 / 8.0 | 8.3 / 8.0 | 8.3 / 8.0 |
| Assay | | | | |
| pH (10% in demineralized water) | 2.9 | 3 | 2.9 | 2.95 |
| Precipitation of lower solid phase in the concentration on 4 months storage | some | none | none | none |
| Emulsion stability in water | fair | good | very good | good |

EXAMPLE 10

Chloridazon and phenmedipham suspensions in mineral oil and with a surfactant component comprising anionic constituents and fatty alcohol The ingredients stated in Table 10 were mixed and ground in the same manner as described in Example 1 above.

Accelerated storage stability test was carried out for only sample 10a. The analysis on chemical stability showed that both chloridazon and phenmedipham were satisfactorily stable.

The addition of co-ethoxylated/propoxylated alkyl phenol (Berol TM 922) and the phosphate ester composition (Berol TM 724 and Gafac TM RE 410) imparted better properties in the samples 10b, 10c and 10d compared to sample 10a with respect to emulsion stability. Even the use of a technical grade of chloridazon with less content of active ingredient yielded a satisfactory result. The optimizations of the surfactant component have a positive influence on the stability shown by a minor precipitation of a lower solid layer which could not be shaken up again. The addition of the co-ethoxylated/propoxylated constituents together with the phosphate ester constituent gave rise to better stability with respect to emulsification when the concentrated products were mixed with water in a ratio of 3% of the concentrated composition in 97% of water.

TABLE 10

| Sample Ingredients | 10a | 10b | 10c | 10d |
|---|---|---|---|---|
| | Amounts, % by weight | | | |
| Oily component | | | | |
| Hydropara 19[1] | 45.6 | 43.8 | 42.3 | 42.2 |
| Surfactant constituent | | | | |
| Hyfatol TM 10[11] (fatty alcohol) | 3.0 | 4.0 | 4.0 | 4.0 |
| Berol TM 272[15] (non-ionic) | 1.2 | — | — | — |
| Berol TM 269[4] (non-ionic) | 8.8 | 8.0 | 8.0 | 8.0 |
| Berol TM 922[16] (non-ionic) | — | 3.0 | 3.0 | 3.0 |
| Berol TM 724[5] (anionic) | 8.5 | 6.2 | 6.2 | 6.2 |
| Gafac TM RE 410[17] (anionic) | — | 2.0 | 2.0 | 2.0 |
| Total surfactant | 21.5 | 23.2 | 23.2 | 23.2 |
| % fatty alcohol of total surfactant composition | 14.0 | 17.2 | 17.2 | 17.2 |
| pH modifier | | | | |
| Monoethanolamine | 2.1 | 1.5 | 1.5 | 1.6 |
| Water | 8 | 8 | 8 | 8 |
| Inorganic filler | | | | |
| Attagel TM 40[7] | — | — | 1.5 | 1.5 |
| Pesticide component | | | | |
| Chloridazon, 84% | 14.5 | — | — | — |
| Chloridazon, 80% ~ pure chloridazon | — / 12.1 | 15.2 / 12.1 | 15.2 / 12.1 | 15.2 / 12.1 |
| Phenmedipham, 97% ~ pure phenmedipham | 8.3 / 8.0 | 8.3 / 8.0 | 8.3 / 8.0 | 8.3 / 8.0 |
| Assay | | | | |
| pH (10% in demineralized water) | 3 | 3 | 3 | 3,2 |
| Content of active ingredient: | | | | |
| Chloridazon | | | | |
| Start | 11.81 | — | — | — |
| After 8 weeks at 50° C. | 11.96 | — | — | — |
| After 20 weeks at 50° C. | 11.78 | — | — | — |
| Phenmedipham | | | | |
| Start | 8.02 | — | — | — |
| After 8 weeks at 50° C. | 8.09 | — | — | — |
| After 20 weeks at 50° C. | 8.00 | — | — | — |
| Precipitation of a lower solid phase after 4 months storage | some | none | none | none |
| Emulsion stability in water | fair | good | good | good |

EXAMPLE 11

Phenmedipham suspension in mineral oil and a surfactant composition comprising fatty alcohol and an anionic surfactant constituent Test samples with compositions illustrated in Table 11 were mixed as describes in Example 1 above, with the exception that Attagel TM was added after the grinding process.

The incorporation of the fatty alcohol (decanol) yields easily flowable compositions which are readily diluted with water. Samples 11b, 11c and 11d are improved compared to 11a by the addition of co-ethoxylated, propoxylated fatty alcohol which is methylated in the terminal OH-group (Rewopall TM MT 2540) and a phosphate ester mixture (Berol TM 725 and Gafac TM RE410).

TABLE 11

| Sample Ingredients | 11a | 11b | 11c | 11d |
|---|---|---|---|---|
| | Amounts, % by weight | | | |
| Oily component | | | | |
| Hydropara 19[1)] | 51.1 | 52 | 51 | 50.5 |
| Surfactant constituent | | | | |
| Hyfatol TM 10[11)] (fatty alcohol) | 1.5 | 1.5 | 1.5 | 1.5 |
| Berol TM 26[3)] (non-ionic) | 5 | 3.5 | 3.5 | 3.5 |
| Berol TM 269[4)] (non-ionic) | 10 | 8 | 8 | 8 |
| Rewopall TM MT 2540[18)] (non-ionic) | — | 1.4 | 1.4 | 1.4 |
| Berol TM 724[5)] anionic) | 9 | 7 | 7 | 7 |
| Gafac TM RE 410[17)] (anionic) | — | 1.6 | 1.6 | 1.6 |
| Total surfactant | 25.5 | 23.0 | 23.0 | 23.0 |
| % fatty alcohol of total surfactant composition | 5.9 | 6.5 | 6.5 | 6.5 |
| pH modifier | | | | |
| Monoethanolamine | 1.9 | 1.5 | 1.5 | 1.5 |
| Water | 4 | 4 | 4 | 4 |
| Inorganic filler | | | | |
| Attagel TM 40[7)] | — | — | 1 | 1.5 |
| Pesticide component | | | | |
| Phenmedipham, 97% ~ pure phenmedipham | 17.5 17 | 19.5 18.9 | 19.5 18.9 | 19.5 18.9 |
| Assay | | | | |
| pH (10% in demineralized water) | 3.2 | 3 | 3 | 3 |
| Viscosity | moderate | moderate | moderate | moderate |
| Dilution with water in the ratio of 3% of concentrate to 97% of water | good | good | good | good |
| Emulsion stability in water | fair | good | good | good |

EXAMPLE 12

Maneb suspensions in an oily, anhydrous component

Test samples with compositions illustrated in Table 12 were prepared in the same manner as described in Example 1.

It appears from storage tests that the amount of the upper clear oily phase greatly depends on the viscosity of the oily composition and thus also on the viscosity of the pure mineral oil. By using a very low-viscous mineral oil/kerosene and as a result of the denser packing of the maneb it will be possible to achieve a product of considerably higher concentration, such as e.g. 300–400 g/l Maneb. This may be of importance in such instances when the content of oil does not have any biological effect but serves as an inactive carrier. The viscosity will moreover depend on the possible presence of a finely ground filler, such as Bentone 36.

The dispersability in water is assayed by filling 100 ml water into a 150 ml beaker and adding 3 ml of the suspension. The ease of distribution in water is observed. The dispersability depends i.a. on the viscosity of the preparation and will often be best when the content of surfactant component is small.

The samples were thoroughly stirred by moving a broad plastic spatula forwards and backwards in the water 10 times. The stability of the water-suspended maneb is observed. Normally, the stability will be best when the amount of surfactant is sufficiently high.

On storing after mixing with water, the oil content will precipitate as an upper phase; normally, this does not have any consequence for the spraying process.

None of the samples illustrated in Table 12 were activated by a strong acid. By varying the ratio between the slightly acidic ampholyte and the slightly alkaline ethoxylated amine, it is possible to adapt the pH-value of the preparation in the range of preferably 7 to 9. The pH-value is measured after dilution of one part of concentrate with nine parts of water.

TABLE 12

| Sample Ingredients | 12a | 12b | 12c | 12d |
|---|---|---|---|---|
| | Amounts, % by weight | | | |
| Oily component | | | | |
| Shell TM HVI 60[9)] | 72.57 | 72.8 | 70.85 | 71.15 |
| Surfactant constituent | | | | |
| Berol TM 26[3)] (non-ionic) | 1.5 | 1.5 | 2.0 | 2.0 |
| Berol TM 269[4)] (non-ionic) | 1.9 | 1.9 | 2.5 | 2.5 |
| Ampholyte SKKP-70[6)] (ampholytical, amino group-containing) | 1.5 | 1.15 | 2.0 | 1.5 |
| Genamin TM C-100[8)] (cationic, amino group-containing) | 0.38 | 0.5 | 0.5 | 0.7 |
| Total surfactant | 4.83 | 4.7 | 6.4 | 6.25 |
| % amino group-containing surfactant of total surfactant composition | 29.6 | 27.7 | 29.7 | 28.0 |
| Inorganic filler | | | | |
| Bentone TM 38[10)] | 0.15 | 0.15 | 0.15 | 0.15 |
| Pesticide component | | | | |
| Maneb, 91% ~ pure maneb | 22.0 20 | 22.0 20 | 22.0 20 | 22.0 20 |
| Assay | | | | |
| pH (10% in demineralized water) | 8.6 | 8.9 | 8.5 | 8.8 |
| Amount of clear upper oily phase after storage | biggest | biggest | smallest | — |
| Dispersability when stirring into water | best | best | worst | worst |
| Stability of suspended Maneb after dilution with water | worst | — | — | best |

EXAMPLE 13

Maneb suspensions in an oily, anhydrous component

Test samples with compositions illustrated in Table 13 were mixed in the same manner as described in Example 1 except that the inorganic filler (Attagel TM) was added to samples 13c and 13d after the grinding process.

In general, maneb has a tendency to precipitate on storage due to its high specific gravity, thus leaving a upper clear oily phase. Maneb suspensions may therefore be difficult to shake and yield uniform concentrates. The addition of the inorganic filler (Attagel TM) improves the ease of re-homogenisation on storage. The addition of propylene glycol assists in maintaining the maneb in stable suspension (shown by decreased amount of clear upper oily phase) on storage. On the other hand, the addition of propylene glycol yields a slightly decreased emulsion stability in water.

Storage tests have been carried out for sample 13a and a significant reduction of active component (ethylene thiourea) on storage was found. Two parallel assays were carried out on two qualities of technical grade maneb (13' and 13").

Biological testing by spraying potatoes was carried out with sample 13a. The sprayed amount was 16 l of concentrate composition per Ha applied for 4 times over a period of 6 weeks. No attack of fungus and no attack of virus (crinkle) could be observed. After the first spraying the plants were slightly affected, but after 2 days the growth of the potato plants was re-established.

TABLE 13

| Sample Ingredients | 13a | 13b | 13c | 13d |
|---|---|---|---|---|
| | Amounts, % by weight | | | |
| Oily component | | | | |
| Shell TM HVI 60[9] | 71.15 | 68.15 | 69.3 | 67.3 |
| Surfactant constituent | | | | |
| Berol TM 26[3] (non-ionic) | 2.5 | 2.5 | 2.5 | 2.5 |
| Berol TM 269[4] (non-ionic) | 2.0 | 2.0 | 2.0 | 2.0 |
| Ampholyte SKKP-70[6] (ampholytical, amino group-containing) | 1.5 | 1.5 | 1.5 | 1.5 |
| Genamin TM C-100[8] (cationic, amino group-containing) | 0.7 | 0.7 | 0.7 | 0.7 |
| Total surfactant | 6.25 | 6.25 | 6.25 | 6.25 |
| % amino group-containing surfactant of total surfactant-composition | 28 | 28 | 28 | 28 |
| Propylene glycol | — | 3 | — | 3 |
| Inorganic filler | | | | |
| Bentone TM 38[10] | 0.15 | 0.15 | — | — |
| Attagel TM 40[7] | — | — | 2 | 1 |
| Pesticide component | | | | |
| Maneb, 91% ~ | 22 | 22 | 22 | 22 |
| pure maneb | 20 | 20 | 20 | 20 |
| Assay | | | | |
| Ease of re-homogenisation to a lower viscosity mixture | some | some | good | some |
| Emulsion stability in water | good | fair | good | fair |
| Analysis | 13' | 13" | | |
| Content of ethylene thiourea: | | | | |
| Start | 0.74 | 0.55 | | |
| After 2 months | 0.53 | — | | |
| After 2¼ months | — | 0.37 | | |
| After 8¼ months | 0.11 | — | | |
| After 9 months | — | 0.05 | | |

EXAMPLE 14

Maneb dispersions in an anhydrous oily phase in which the surfactant component comprises an amino group-containing surfactant and optionally a fatty alcohol as stabilizing constituents Test samples with compositions illustrated in Table 14 were prepared in the same manner as described in Example 1.

Samples 14a and 14b comprised mineral oil as the oily component, and sample 14c and 14d comprised synthetic ester oil (2-ethyl hexyl stearate) as the oily component.

Visual examination showed that the addition of Emulsogen EL (ethoxylated castor oil) in the samples 14a and 14c gives a small increase in the emulsion stability.

By replacing a part of the oily component by Hyfatol TM 10 (fatty alcohol, n-decanol) so that the surfactant composition comprises both an amino group-containing surfactant and the fatty alcohol as stabilizing constituents, the physical property of sample 14b has been slightly improved compared to sample 14a and substantially increased for sample 14d compared to sample 14c.

The addition of Emulsogen EL improves the emulsion stability which is further improved by the addition of the fatty alcohol.

TABLE 14

| Sample Ingredients | 14a | 14b | 14c | 14d |
|---|---|---|---|---|
| | Amounts, % by weight | | | |
| Oily component | | | | |
| Shell TM HVI 60[9] | 66.8 | 65.8 | — | — |
| Radia TM 7131[21] | — | — | 63.8 | 58.8 |
| Surfactant constituent | | | | |
| Hyfatol TM 10[11] (fatty alcohol) | — | 1 | — | 5 |
| Berol TM 26[3] (non-ionic) | 2.5 | 2.5 | 2.5 | 2.5 |
| Berol TM 269[4] (non-ionic) | 2 | 2 | 2 | 2 |
| Emulsogen EL[19] (non-ionic) | 1.5 | 1.5 | 1.5 | 1.5 |
| Ampholyte SKKP-70[6] (ampholytical, amino group-containing) | 1.5 | 1.5 | 1.5 | 1.5 |
| Genamin TM C-100[8] (cationic, amino group-containing) | 0.7 | 0.7 | 0.7 | 0.7 |
| Total surfactant | 7.75 | 8.75 | 7.75 | 12.75 |
| % amino group-containing surfactant of total surfactant composition | 22.5 | 20 | 22.5 | 13.7 |
| % fatty alcohol of total surfactant composition | — | 11.5 | — | 39.2 |
| Inorganic filler | | | | |
| Attagel TM 40[7] | 3 | 3 | 6 | 6 |
| Pesticide component | | | | |
| Maneb, 91% | 22 | 22 | 22 | 22 |
| ~ pure maneb | 20 | 20 | 20 | 20 |
| Assay | | | | |
| pH, 10% in demineralized water | 7.8 | 7.8 | 8.1 | 8.1 |
| Ease of distribution in water by dilution | good | good | good | good |
| Emulsion stability in water | fair | fair/good | fair | good |

EXAMPLE 15

Glyphosate dispersions in an oily component and with a non-ionic and amino group-containing ionic surfactant constituent in the surfactant component Test samples with compositions illustrated in Table 15 were mixed and ground in the same manner as described in Example 1 except that the Attagel TM was added after the grinding process.

The use of non-ionic surfactants and ionic amino group-containing surfactants yields good stability in the compositions which is seen by the fact that there is only a limited setting of the finely ground glyphosate. The compositions are easy to re-homogenize by a gentle shaking, and addition of the inorganic filler (Attagel TM) improves the re-homogenisation.

When mixed with water all the compositions easily form homogeneous spray liquids.

TABLE 15

| Sample Ingredients | 15a | 15b | 15c | 15d |
|---|---|---|---|---|
| | Amounts, % by weight | | | |
| Oily component | | | | |
| Hydropara TM 19[1] | 46 | 46.2 | 45.2 | 44.2 |
| Surfactant constituent | | | | |
| Berol TM 26[3] (non-ionic) | 7 | 6 | 6 | 6 |
| Berol TM 269[4] (non-ionic) | 12 | 13 | 13 | 13 |
| Genamin TM C-100[8] (cationic, amino group-containing) | 2.8 | 2.8 | 2.8 | 2.8 |
| Ampholyte SKKP-70[6] (ampholytical, amino group-containing) | 4.8 | 4.7 | 4.7 | 4.7 |
| Total surfactant | 25.2 | 25.1 | 25.1 | 25.1 |
| % amino group-containing surfactant of total surfactant composition | 24.4 | 24.2 | 24.2 | 24.2 |

TABLE 15-continued

| Sample Ingredients | 15a | 15b | 15c | 15d |
|---|---|---|---|---|
| | Amounts, % by weight | | | |
| pH modifier | | | | |
| Maleic acid anhydride | 1.4 | — | — | — |
| Perchloric acid 70% | — | 2.3 | 2.3 | 2.3 |
| Inorganic filler | | | | |
| Attagel TM 40[(7)] | 1 | — | 1 | 2 |
| Pesticide component | | | | |
| Glyphosate, 96% | 25 | 25 | 25 | 25 |
| ~ pure glyphosate | 24 | 24 | 24 | 24 |
| Assay | | | | |
| pH, 10% in demineralized water | 2.1 | 1.9 | 1.9 | 1.9 |
| Tendency to form a re-homogenisable sediment in the concentrate | some | some | little | little |
| Ease of distribution in water by dilution | good | good | good | good |

EXAMPLE 16

Glyphosate compositions in oil and comprising a mixture of non-ionic and anionic surfactants Test samples with compositions illustrated in Table 16 are prepared in the same manner as described in Example 1 except that the Attagel TM was added after the grinding process.

The addition of Attagel TM leads to a decreased tendency to form sediments. Small amounts (less than 1%) of decanol (Hyfatol TM) leads to increased tendency to form sediments, whereas large amounts (about 2%) improve the stability (i.e. reduce the tendency to form sediments). The decanol constituent (in an amount 1.5-2%) improves the ease of dilution with water and minimizes the formation of intermediary gel-like lumps in the liquid ready to be sprayed.

Compositions with a mixture of phosphate esters (Berol TM 724 and Gafac TM RE 410) are easier to disperse in water than compositions comprising only one phosphate ester; furthermore, an increased stability in the emulsion is achieved with the use of more than one phosphate ester.

The aqueous solutions become more viscous on standing, thus leading to increased adhesion to the plant leaves and to a reduced drifting by the wind during the spraying on the fields.

TABLE 16

| Sample Ingredients | 16a | 16b | 16c | 16d |
|---|---|---|---|---|
| | Amounts, % by weight | | | |
| Oily component | | | | |
| Hydropara TM 19[(1)] | 50.1 | 51.5 | 50.6 | 49.7 |
| Surfactant constituent | | | | |
| Berol TM 269[(4)](non-ionic) | 14 | 9 | 9 | 9 |
| Berol TM 724[(5)](anionic) | 8 | 6 | 6 | 6 |
| Gafac TM RE 410[(17)](anionic) | — | 1.5 | 1.5 | 1.5 |
| Hyfatol TM 10[(11)] (fatty alcohol, decanol) | 1.5 | — | 0.9 | 1.8 |
| Total surfactant | 23.5 | 16.5 | 17.4 | 18.3 |
| % fatty alcohol of total surfactant composition | 6.3 | — | 5.2 | 9.8 |
| pH modifier | | | | |
| Monoethanolamine | 1.4 | 1 | 1 | 1 |
| Inorganic filler | | | | |
| Attagel TM 40[(7)] | — | 6 | 6 | 6 |
| Pesticide component | | | | |
| Glyphosate, 96% | 25 | 25 | 25 | 25 |
| ~ pure glyphosate | 24 | 24 | 24 | 24 |
| Assay | | | | |
| pH, 10% in demineralized water | 2 | 2 | 2 | 2 |
| Tendency to form a redispersable sediment in the concentrate | very | little | some | very little |
| Ease of dispersion in water | fair | fair | fair | very good |
| Emulsion stability in water | fair | good | good | good |

EXAMPLE 17

Glyphosate compositions may be examined for washing off at a laboratory test carried out in the following manner. The following laboratory test used for glyphosate compositions whilst not being identical to the conditions in nature may be used as an indication of the tendency for a composition to be removed from the leaf by water.

The compositions were applied on glass sheets treated with wax.

The glass sheets were 20×30 cm. The application of wax took place by distributing 1 g of a 40% soft bees' wax thinned with kerosene, by means of a flat plastic spatula. The glass sheets were heated to 80° C. to provide a thin uniform coating of wax and were stored for 20 hours at 80° C. to ensure removal of the kerosene. After cooling the sheets were ready to be used.

The test solutions were prepared by dissolving ca. 500 mg of the glyphosate compositions in 100 ml of water. 5 ml were pipeted onto the glass sheets. The comparison product, "Roundup TM", was difficult to distribute on the wax-treated glass sheet as seen by its uneven distribution. The compositions according to the invention were easier to distribute evenly. After the application the sheets were left to dry for about 20 hours at room temperature.

The leaching was performed by vertically dipping the glass sheets for 60 seconds in tap water (15° C.). When the glass sheets had been taken out of the water, they were washed with a solution of 2% propylamine, 10% ethanol and 88% water to dissolve the glyphosate composition adhering to the waxed surface, and analysis for glyphosate was performed.

It appears from the analysis results that for the known composition (Roundup TM) only 3.3% glyphosate could be found on the waxed glass sheet, whereas 46 and 61%, respectively, could be found for the samples 15a and 16d (prepared according to Examples 15 and 16, respectively). It is assumed that the residual amount of Roundup TM would have been even smaller if the solution has been more evenly distributed on the glass sheets.

TABLE 17

| Composition | Roundup TM * | Sample 15a | Sample 16d |
|---|---|---|---|
| Amount of composition, g | 1.5 | 2 | 2 |
| % of glyphosate in composition | 30.6 | 24 | 24 |
| Pipeted amount of glyphosate (in mg) | 23 | 24 | 24 |
| Analysis on unwashed glass sheet (in mg) | 19.9 | 21 | 20 |
| Analysis on washed glass sheet I (in mg) | 1.1 | 11.1 | 12.6 |
| Analysis on washed glass sheet II (in mg) | 0.2 | 8.2 | 11.7 |
| % of glyphosate I not removed by washing | 5.5 | 53 | 63 |
| % of glyphosate II not | 1.0 | 39 | 59 |

TABLE 17-continued

| Composition | Roundup TM * | Sample 15a | Sample 16d |
|---|---|---|---|
| removed by washing | | | |
| Mean of % of glyphosate not removed by washing | 3.3 | 46 | 61 |
| Surface tension of a 1% aqueous solution (mN/m) | 40 | 30 | 29.5 |

*Registered commercial product from Monsanto and comprising 30.6% glyphosate as propylamine salt

EXAMPLE 18

Glyphosate dispersions with a high content of glyphosate

Test samples with compositions illustrated in Table 18 were prepared in the same manner as described in Example 1.

Sample 18a has a slight tendency to form sediment on standing, but all compositions can easily be shaken into homogenous dispersions even after standing for several months.

All samples are easy to disperse in water without a detrimental tendency to the formation of gel lumps. All emulsions are stable.

TABLE 18

| Sample Ingredients | 18a | 18b | 18c | 18d |
|---|---|---|---|---|
| | \multicolumn{4}{c}{Amounts, % by weight} | | | |
| Oily component | | | | |
| Hydropara TM HVI 19[1] | — | 37 | 32.45 | 28.55 |
| Gravex TM 19[20] | 32 | — | — | — |
| Surfactant constituent | | | | |
| Hyfatol TM 10[11] (fatty alcohol) | — | — | 2.1 | 2.5 |
| Berol TM 26[3](non-ionic) | — | 4.8 | — | — |
| Berol TM 269[4](non-ionic) | 10.8 | 10.4 | 9.5 | 11.3 |
| Berol TM 724[5](anionic) | — | — | 6.3 | 7.5 |
| Gafac TM RE 410[17](anionic) | — | — | 1.6 | 1.9 |
| Ampholyte SKKP-70[6] (ampholytical, amino group-containing) | 4.2 | 3.7 | — | — |
| Genamin TM C-100[8] (cationic, amino group-containing) | 2.5 | 2.3 | — | — |
| Total surfactant | 16.2 | 20.1 | 19.5 | 23.2 |
| % amino group-containing surfactant of total surfactant composition | 33.5 | 23.3 | — | — |
| % fatty alcohol of total surfactant composition | — | — | 10.8 | 10.8 |
| pH modifier | | | | |
| Perchloric acid 70% | 2 | 1.8 | — | — |
| Monoethanolamine | — | — | 1.05 | 1.25 |
| Pesticide component | | | | |
| Glyphosate, 96% | 48.5 | 40 | 47 | 47 |
| ~ pure glyphosate | 46.6 | 38.4 | 45.1 | 45.1 |
| Assay | | | | |
| pH, 10% in demineralized water | 1.9 | 2.1 | 2.0 | 2.0 |
| Tendency to form a redispersable sediment in the concentrate | some | little | little | little |
| Ease of distribution in water by dilution | good | fair/good | good | good |
| Emulsion stability in water | good | fair/good | good | good |

EXAMPLE 19

Phenmedipham dispersions with different types of oil as oily component

Test samples with compositions as illustrated in Table 19 were prepared in the same manner as described in Example 1.

Sample 19a comprised 1% hydroquinone as absorbant for UV light. Addition of hydroquinone will delay the decomposition of phenmedipham after spraying on the beet plants. Normally, hydroquinone has a detrimental effect on concentrated compositions. This problem has been solved by adding 1.5% by weight Hyfatol TM 10 (n-decanol) as the stabilizing constituent in the surfactant composition. The dispersability in water and the emulsion stability was slightly increased.

Samples 19b, 19c and 19d could all easily be dispersed in water and formed fairly stable emulsions in the diluting water.

TABLE 19

| Sample Ingredients | 19a | 19b | 19c | 19d |
|---|---|---|---|---|
| | \multicolumn{4}{c}{Amounts, % by weight} | | | |
| Oily component | | | | |
| Hydropara TM HVI 19[1] | 56 | — | — | — |
| Gravex TM 19[20] | — | — | 52.5 | 43.6 |
| Radia TM 7131[21] | — | 51 | — | — |
| Refined rape oil | — | — | — | 15 |
| Surfactant constituent | | | | |
| Hyfatol TM 10[11] (fatty alcohol) | 1.5 | 1.5 | 1.5 | 2 |
| Berol TM 26[3](non-ionic) | 0.5 | 1 | 1 | — |
| Berol TM 269[4](non-ionic) | 10.5 | 10.5 | 10.5 | 11.5 |
| Berol TM 724[5](anionic) | — | 7 | 7 | 7 |
| Gafac TM RE 410[17](anionic) | — | 1.6 | 1.6 | 1.6 |
| Rewopal MT TM 2540[18] (non-ionic) | 2 | 1.4 | 1.4 | 2 |
| Ampholyte SKKP-70[6] (ampholytical, amino group-containing) | 2.7 | — | — | — |
| Genamin TM C-100[8] (cationic, amino group-containing) | 1.5 | — | — | — |
| Total surfactant | 17.9 | 23 | 23 | 24.1 |
| % amino group-containing surfactant of total surfactant composition | 19 | — | — | — |
| % fatty alcohol of total surfactant composition | 10.8 | 6.5 | 6.5 | 8.3 |
| pH modifier | | | | |
| Perchloric acid 70% | 1.3 | — | — | — |
| Monoethanolamine | — | 1.5 | 1.5 | 1.5 |
| Water | 4 | 4 | 4 | 4 |
| Inorganic filler | | | | |
| Attagel TM 40[7] | 1.5 | 3 | 1.5 | 4 |
| UV-absorber | | | | |
| Hydroquinone | 1 | — | — | — |
| Pesticide component | | | | |
| Phenmedipham, 97% | 17.5 | 17.5 | 17.5 | 7.8 |
| ~ pure phenmedipham | 17 | 17 | 17 | 7.5 |
| Assay | | | | |
| pH, 10% in demineralized water | 3 | 3.1 | 2.9 | 2.9 |
| Stability of concentrate | good | good | good | good |
| Ease of distribution in water by dilution | good | good | good | good |
| Emulsion stability in water | good | good | good | good |

We claim:

1. A pesticidal concentrate composition which can be reconstituted with water to form a storage-stable pesticidal emulsion useful for spraying, the emulsion being substantially free of gels, lumps, precipitates, and sediments, said pesticidal concentrate composition comprising:

(a) 1–55% by weight of a solid particulate or liquid pesticidal component, which is dispersed in (b) and (c);

(b) 20–90% by weight of an oily component selected from the group consisting of petroleum fractions, vegetable oils, and esters of mono- or polyalcohols having 2–6 hydroxy functions with mono- or polycarboxylic acids, the oily component being liquid at normal temperatures and immiscible with water in a ratio of 1:10–10:1 by weight and comprising at least 67% by weight of hydrocarbyl or hydrocarbylene, based on the total chemical composition of the oily component; and (c) 1–45% by weight of surfactants, the surfactants comprising at least one non-ionic surfactant and at least one stabilizing constituent which is a fatty alcohol selected from the group consisting of mono- and dialcohols having a $C_{5-30}$ hydrocarbyl or hydrocarbylene chain, the stabilizing constituent(s) being present in an amount of 6–60% by weight based on the total amount of surfactant(s), including stabilizing constituent(s), present.

2. A composition according to claim 1, wherein the stabilizing constituent further comprises an amino compound comprising a $C_{5-30}$ hydrocarbyl or hydrocarbylene chain.

3. A composition according to claim 1, wherein the fatty alcohol contains 7–22 carbon atoms.

4. A composition according to claim 3, wherein the fatty alcohol contains 9–18 carbon atoms.

5. A composition according to claim 4, wherein the fatty alcohol contains 10 carbon atoms.

6. A composition according to claim 5, wherein the fatty alcohol is decanol.

7. A composition according to claim 6, wherein the fatty alcohol is n-decanol.

8. A composition as recited in claim 1, wherein said surfactants further comprise at least one anionic surfactant.

9. A composition as recited in claim 1, wherein the hydrocarbyl or hydrocarbylene chain of the amino compound comprises 7–22 carbon atoms.

10. A composition as recited in claim 1, wherein the hydrocarbyl or hydrocarbylene chain of the amino compound comprises 9–18 carbon atoms.

11. A composition as recited in claim 1, wherein the amount of the stabilizing constituent constitutes 8–45% by weight of the total weight of the surfactant(s), including the stabilizing constituent(s) which are present.

12. A composition as recited in claim 1, wherein the amount of the stabilizing constituent constitutes 12–35% by weight of the total weight of the surfactant(s), including the stabilizing constituent(s) which are present.

13. A composition as recited in claim 2, wherein the $C_{5-30}$ hydrocarbyl or hydrocarbylene chain of the amino compound is substituted by at least one substituent selected from the group consisting of carboxy, sulphonic acid, phosphonic acid, (poly)oxyalkylene and hydroxy.

14. A composition as recited in claim 2, wherein the amino group-containing compound is a $C_{7-22}$ hydrocarbyl or hydrocarbylene amine, which is substituted by at least one substituent selected from the group consisting of carboxy, sulphonic acid, phosphonic acid, (poly)oxyalkylene and hydroxy.

15. A composition as recited in claim 13, wherein the amino compound is an ampholyte.

16. A composition according to claim 2, wherein the total amount of the amino compound and the fatty alcohol which are present constitutes 6–60% by weight of the total weight of the surfactant(s), including the stabilizing constituent(s).

17. A composition according to claim 1, wherein the stabilizing constituents further comprise at least two different amino compounds comprising a $C_{5-30}$ hydrocarbyl or hydrocarbylene chain, the total amount of the amino compounds and the fatty alcohol constituting 6–60% by weight of the total weight of the surfactant(s), including the stabilizing constituent(s); with the proviso that at least one of the amino compounds carries, in addition to its amino group, at least one other substituent selected from the group consisting of carboxy, sulphonic acid, phosphonic acid, (poly)oxyethylene, (poly)oxypropylene and hydroxy.

18. A composition as recited in claim 2, wherein the amount of the amino compound constitutes at least 50% by weight of the total amount of ionic surfactant(s) present in the composition.

19. A composition as recited in claim 2, wherein the amount of the amino compound constitutes at least 70% by weight of the total amount of ionic surfactant(s) present in the composition.

20. A composition as recited in claim 2, wherein the amount of the amino compound constitutes at least 100% by weight of the total amount of ionic surfactant(s) present in the composition.

21. A composition as recited in claim 2, which further comprises a strong acidic component.

22. A composition as recited in claim 21, wherein the amount of the acidic component is 25–400%, on a molar basis, of the amount of the amino compound.

23. A composition as recited in claim 21, wherein the amount of the acidic component is 50–250%, on a molar basis, of the amount of the amino compound.

24. A composition as recited in claim 21, wherein the amount of the acidic component is 75–175%, on a molar basis, of the amount of the amino compound.

25. A composition as recited in claim 1, which contains a non-ionic surfactant constituent selected from the group consisting of block polymers which are condensates of polyoxyethylene and polyoxypropylene; ethoxylated, propoxylated and co-ethoxylated/propoxylated fatty alcohols; ethoxylated, propoxylated and co-ethoxolated/propoxylated mono-, di- and trialkyl phenols; and mono-, di- and poly(carboxyl) fatty acid esters in which the alcohol moiety is selected from the group consisting of polyoxyethylene alcohol, polyoxypropylene alcohol, polyoxyalkylene alcohols combined from different glycols, polyalcohols, ethoxylated polyalcohols, propoxylated polyalcohols, and co-ethoxylated/propoxylated polyalcohols.

26. A composition as recited in claim 25, which comprises at least two non-ionic surfactants which have different HLB values.

27. A pesticidal composition as recited in claim 1, wherein the pesticidal component (a) comprises a herbicide selected from the group consisting of derivatives of urea, derivatives of carboxylic acid esters, derivatives of amino acids, derivatives of diphenylethers, derivatives of phenylcarbamates, derivatives of thiocarbamates, derivatives of s-triazine, derivatives of astriazinones, derivatives of phenoxy acetic acids, derivatives of phenoxy propionic acids, 3-isopropyl-1(H)-benzo-2,1,3-thiadiazin-4-one-2,2-dioxid; 3-cyclohexyl-6-dimethylamino-1-methyl-1,3,5-triazine-2,4(1H, 3H)-dione;

1-(2-chlorophenylsulphonyl)-3-(4-methoxy-6-methyl-1,3,5-triazine-2-yl)urea; 5-amino-4-chloro-2-phenyl-3(2H)pyridazinone; (±)-2-ethoxy-2,3-dihydro-3,3-dimethylbenzofuran-5-yl methanesulphonate and 7-chloro-3-methyl-quinoline-8-carboxylic acid.

28. A pesticidal composition according to claim 27, wherein the herbicide is selected from the group consisting of phenmedipham, metamitron and chloridazon.

29. A pesticidal composition as recited in claim 28, which contains both phenmedipham and metamitron, the weight ratio of phenmedipham to metamitron being in the range of 1:2–1:8.

30. A pesticidal composition as recited in claim 28, which contains both phenmedipham and metamitron, the weight ratio of phenmedipham to metamitron being in the range of 1:3–1:6.

31. A pesticidal composition as recited in claim 28, which contains both phenmedipham and metamitron, the weight ratio of phenmedipham to metamitron being in the range of 1:4–1:6.

32. A pesticidal composition as recited in claim 1, wherein the pesticidal component (a) comprises a fungicide selected from the group consisting of dithiocarbamates, 2-benzimidazole carbamates and dithioureido benzene derivatives.

33. A pesticidal composition as recited in claim 1, which further comprises water in an amount of 0.1–40% by weight, based on the total composition.

34. A pesticidal composition as recited in claim 1, which further comprises water in an amount of 0.2–20% by weight, based on the total composition.

35. A pesticidal composition as recited in claim 1, which further comprises water in an amount of 0.5–10% by weight, based on the total composition.

36. A pesticidal composition as recited in claim 1, which further comprises water in an amount of 0.1–20% by weight, based on the total composition.

37. An oil-in-water emulsion, comprising:
(a) up to 10% by weight of an oily phase constituted by a pesticidal composition as claimed in claim 1,
(b) 90–99.0% by volume of water.

38. An oil in water emulsion as recited in claim 36, further comprising an inorganic filler.

39. A pesticidal composition as recited in claim 1, in which the pesticidal component is selected from the group consisting of phenmedipham, desmedipham and chloridazon.

40. A composition as recited in claim 39, in which the surfactants further comprise at least one anionic surfactant.

41. A composition as recited in claim 40, wherein the anionic surfactant is an acidic phosphate ester.

42. A composition according to claim 40, wherein the anionic surfactant is an acidic phosphate ester selected from the group consisting of:
mono- and diesters of ethoxylated, propoxylated and co-ethoxylated/propoxylated fatty alcohols; mono-, di and trialkyl phenols, and di- and tristyryl phenols; and non-ethoxylated $C_{4-18}$ fatty alcohols.

43. A composition according to claim 40, wherein the anionic surfactant is selected from the group consisting of alkyl sulphonic acids, aryl sulphonic acids, arylalkyl sulphonic acids, alkylaryl sulphonic acids and phosphonic acids.

44. A pesticidal concentrate composition as recited in claim 1 in which the pesticidal component is a dithiocarbamate.

45. A pesticidal composition as recited in claim 44, wherein the surfactants further comprise an amino compound which is present in an amount of at least 4% by weight, based on the total amount of the surfactant(s), including the stabilizing constituent(s).

46. A pesticidal composition as recited in claim 44 in which the dithiocarbamate is present in an amount of 5–50% by weight.

47. A pesticidal composition as recited in claim 46, wherein the surfactants further comprise an amino compound which is present in an amount of at least 4% by weight based on the total amount of the surfactant(s) and the stabilizing constituent(s).

48. A pesticidal concentrate composition as recited in claim 1 in which the pesticidal component is a finely ground glyphosate.

49. A composition according to claim 48, wherein at least 50% by weight of the finely ground glyphosate has a particle size of less than $5\mu$.

50. A composition according to claim 48, the composition having a pH of less than 4 upon dilution with one part by volume of water.

51. A composition as recited in claim 48, the composition having a pH less than 3.5 upon dilution with 1 part by volume of water.

52. A composition as recited in claim 48, the composition having a pH less than 3 upon dilution with 1 part by volume of water.

53. A composition according to claim 48, wherein the surfactants comprise a non-ionic surfactant and an ionic surfactant.

54. A composition according to claim 53, wherein the non-ionic surfactant is selected from the group consisting of block polymers, which are condensates of polyoxyethylene and polyoxypropylene; ethoxylated, propoxylated and co-ethoxylated/propoxylated fatty alcohols; ethoxylated, propoxylated and co-ethoxylated/propoxylated mono-, di- and trialkyl phenols; and mono-, di- and poly(carboxyl) fatty acid esters in which the alcohol moiety is selected from the group consisting of polyoxyethylene alcohol, polyoxypropylene alcohol, polyoxyalkylene alcohols combined from different glycols, polyalcohols, ethoxylated poly-alcohols, propoxylated polyalcohols and co-ethoxylated/propoxylated polyalcohols.

55. A composition according to claim 53, wherein the ionic surfactant comprises at least one amino group-containing surfactant which is a $C_{5-30}$ hydrocarbyl or hydrocarbylene amine.

56. A composition according to claim 53, wherein the ionic surfactant comprises at least one amino group-containing surfactant which is a $C_{5-30}$ hydrocarbyl or hydrocarbylene amine which is unsubstituted or substituted by at least one functional substituent selected from the group consisting of carboxy, sulphonic acid, phosphonic acid, (poly)oxyethylene, (poly)oxypropylene and hydroxy.

57. A composition according to claim 53, wherein the ionic surfactant comprises at least one anionic surfactant.

58. A composition according to claim 57, wherein the anionic surfactant is an acidic phosphate ester selected from the group consisting of mono- and diesters of ethoxylated, propoxylated and co-ethoxylated/propoxylated fatty alcohols, mono-, di-and trialkyl phenols and mono-, di- and tristyryl phenols; and mono- and diesters of non-ethoxylated $C_{4-18}$ fatty alcohols.

59. A composition according to claim 57, wherein the anionic surfactant is selected from the group consisting of alkyl sulphonic acids, aryl sulphonic acids, arylalkyl sulphonic acids, alkylaryl sulphonic acids and phosphonic acids.

60. A composition as recited in claim 53, wherein the ionic surfactant comprises at least one amino group-containing surfactant which is a $C_{7-22}$ hydrocarbyl or hydrocarbylene amine.

61. A composition as recited in claim 53, wherein the ionic surfactant comprises at least one amino group-containing surfactant which is a $C_{7-22}$ hydrocarbyl or hydrocarbylene amine substituted by at least one functional substituent selected from the group consisting of carboxy, sulphonic acid, phosphonic acid, (poly)oxyethylene, (poly)oxypropylene and hydroxy.

62. A composition as recited in claim 53, wherein the ionic surfactant comprises at least one amino group-containing surfactant which is a $C_{9-18}$ hydrocarbyl or hydrocarbylene amine.

63. A composition as recited in claim 53, wherein the ionic surfactant substituent comprises at least one amino group-containing surfactant which is a $C_{9-18}$ hydrocarbyl or hydrocarbylene amine substituted by at least one functional substituent selected from the group consisting of carboxy, sulphonic acid, phosphonic acid, (poly)oxyethylene, (poly)oxypropylene and hydroxy.

* * * * *